US008975248B2

(12) United States Patent  
Zaknoen et al.

(10) Patent No.: US 8,975,248 B2  
(45) Date of Patent: Mar. 10, 2015

(54) COMBINATIONS OF THERAPEUTIC AGENTS FOR TREATING CANCER

(75) Inventors: Sara Zaknoen, Hoboken, NJ (US); Margaret Ma Woo, Raritan, NJ (US); Richard William Versace, Wanaque, NJ (US); Claudio Pisano, Aprilia (IT); Loredana Vesci, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 1206 days.

(21) Appl. No.: 11/720,776

(22) PCT Filed: Dec. 13, 2005

(86) PCT No.: PCT/US2005/044993  
§ 371 (c)(1),  
(2), (4) Date: Jun. 4, 2007

(87) PCT Pub. No.: WO2006/065780  
PCT Pub. Date: Jun. 22, 2006

(65) Prior Publication Data  
US 2010/0028338 A1 Feb. 4, 2010

Related U.S. Application Data

(60) Provisional application No. 60/636,439, filed on Dec. 15, 2004.

(51) Int. Cl.  
*A61K 31/47* (2006.01)  
*A61K 31/282* (2006.01)  
*A61K 33/24* (2006.01)  
*A61K 39/395* (2006.01)  
*A61K 31/427* (2006.01)  
*A61K 31/53* (2006.01)  
*A61K 31/555* (2006.01)  
*A61K 31/4745* (2006.01)  
*A61K 31/337* (2006.01)  
*A61K 45/06* (2006.01)

(52) U.S. Cl.  
CPC ............... *A61K 45/06* (2013.01); *A61K 31/282* (2013.01); *A61K 33/24* (2013.01); *A61K 39/395* (2013.01); *A61K 31/427* (2013.01); *A61K 31/53* (2013.01); *A61K 31/555* (2013.01); *A61K 31/4745* (2013.01); *A61K 31/337* (2013.01)  
USPC ...................... 514/187; 514/253.06

(58) Field of Classification Search  
CPC .... C07D 217/00; C07D 215/00; A61K 31/47; A61K 31/4745  
See application file for complete search history.

(56) References Cited

U.S. PATENT DOCUMENTS

| 7,105,492 B2* | 9/2006 | Dallavalle et al. | 514/25 |
| 2002/0103141 A1* | 8/2002 | McKearn et al. | 514/43 |
| 2004/0018988 A1 | 1/2004 | Dallavalle et al. | |
| 2004/0116407 A1* | 6/2004 | Borisy et al. | 514/217 |
| 2005/0272755 A1* | 12/2005 | Denis et al. | 514/283 |

FOREIGN PATENT DOCUMENTS

| EP | 0715854 | 9/2003 | |
| JP | 2002-539128 | 11/2002 | |
| JP | 2004-529150 | 9/2004 | |
| JP | 2008-169825 | 7/2008 | |
| WO | WO 00/53607 A1 * | 9/2000 | C07D 491/22 |
| WO | WO 02/085459 | 10/2002 | |
| WO | WO-03/013541 | 2/2003 | |
| WO | WO-03/037897 | 5/2003 | |
| WO | WO-2004/083214 | 9/2004 | |
| WO | WO-2004/103274 | 12/2004 | |
| WO | WO 2004/103358 | 12/2004 | |
| WO | WO-2006/065780 | 6/2006 | |

OTHER PUBLICATIONS

Petrangolini et al. (Molecular Cancer Research 2003; 1: 863-870).*  
Kao et al. (J. Nucl. Med. 2001 ; 42 : 17-20).*  
Byers, T. (CA Cancer Journal, vol. 49, No. 6, Nov./Dec. 1999).*  
Doctor's Guide, Personal Edition (FDA Approves Avastin (Bevacizumab, rhuMAB-VEGF) for Treatment of Metastatic Colon or Rectal Cancer, Feb. 27, 2004).*  
MeSH (ST1481, Sep. 4, 2001).*  
MeSH (erlotinib, Nov. 22, 1999).*  
MeSH (everolimus, Aug. 11, 1997).*  
MeSH (epothilone B, Jun. 28, 1995).*  
PubChem Compound (AEE 788 Dec. 8, 2010).*  
Velcade® (bortezomib, Takeda/Millennium, Aug. 23, 2010).*  
MeSH (cetuximab, Jul. 26, 2000).*  
Dorland's Medical Dictionary for Healthcare Consumers (glioblastoma, Elsevier, 2007).*  
MeSH (bortezomib, Sep. 4, 2001).*  
Non-small Cell Lung Cancer Collaborative Group (BMJ Oct. 7, 1995 311:899-909).*  
Langer et al. (Europ. J. Cancer 2000 36: 183-193).*  
International Search Report and Written Opinion for PCT/US2005/044993 mailed Jul. 3, 2006.  
Search Report and Written Opinion received for Singapore Appln. No. 200704032-2 mailed Sep. 30, 2008.  
Sekikawa et al., "Combination chemotherapy of a novel pyrazoloacridone derivative, KW-2170, and SN-38: The synergy and mechanisms," Proceedings of the American Association for Cancer Research Annual Meeting, vol. 42, p. 252 (2001) and $92^{nd}$ Annual Meeting of the American Association for Cancer Research (2001).

(Continued)

Primary Examiner — Peter J Reddig  
(74) Attorney, Agent, or Firm — Foley & Lardner LLP

(57) ABSTRACT

A combination therapy for treating patients suffering from proliferative diseases or diseases associated with persistent angiogenesis is disclosed. The patient is treated with a camptothecin derivative and one or more chemotherapeutic agents selected from a microtubule active agent; an alkylating agent; an anti-neoplastic anti-metabolite; a platin compound; a topoisomerase II inhibitor; a VEGF inhibitor; a tyrosine kinase inhibitor; an EGFR kinase inhibitor; an mTOR kinase inhibitor; an insulin-like growth factor I inhibitor; a Raf kinase inhibitor; a monoclonal antibody; a proteasome inhibitor; a HDAC inhibitor; and ionizing radiation.

11 Claims, No Drawings

(56) References Cited

OTHER PUBLICATIONS

Sartore-Bianchi et al., "The combination of the novel camptothecin analogue Gimatecan (ST1481) plus the proteasome inhibitor PS341 produces an enhanced pro-apoptotic effect in a malignant mesothelioma cell line," Proceedings of the American Association for Cancer Research Annual Meeting, vol. 44, pp. 742-743 (2003) & 94th Annual Meeting of the American Association for Cancer Research (2003).

Perego et al., "511 Potentiation of cell sensitivity to the DNA topoisomerase I inhibitor gimatecan by TRAIL in prostate carcinoma cells," European Journal of Cancer, Supplement, vol. 2(8), p. 156 (2004).

Boulay, et al., "Antitumor Efficacy of Intermittent Treatment Schedules with the Rapamycin Derivative RAD001 Correlates with Prolonged Inactivation of Ribosomal Protein S6 Kinase 1 in Peripheral Blood Mononuclear Cells," Cancer Research 2004; 64: 252-261.

Notice of Preliminary Rejection (English Translation) in Korean Application No. 10-2007-7013401 dated Apr. 24, 2013.

Traxler, et al., "AEE788: A Dual Family Epidermal Growth Factor Receptor/ErbB2 and Vascular Endothelial Growth Factor Receptor Tyrosine Kinase Inhibitor with Antitumor and Antiangiogenic Activity," Cancer Research 2004; 64: 4931-4941.

Xu et al., "Progress of the Research on Epothilones as New Natural Anti-tumor Drugs," Chin Pharm J., Sep. 2003, vol. 38, No. 9, pp. 648-651. (English abstract included).

Second Office Action in Chinese Application No. 200580042979.8 received Jan. 15, 2010 (English translation included—6 pages.

\* cited by examiner

COMBINATIONS OF THERAPEUTIC AGENTS FOR TREATING CANCER

This application claims benefit of U.S. Provisional Application No. 60/636,439, filed Dec. 15, 2004.

The invention relates to a method of preventing or treating proliferative diseases or diseases that are associated with or triggered by persistent angiogenesis in a mammal, particularly a human, with a combination of pharmaceutical agents which comprises:

(a) a camptothecin derivative; and
(b) one or more chemotherapeutic agents.

The invention further relates to pharmaceutical compositions comprising:

(a) a camptothecin derivative;
(b) one or more chemotherapeutic agents; and
(c) a pharmaceutically acceptable carrier.

The present invention further relates to a commercial package or product comprising:

(a) a pharmaceutical formulation of a camptothecin derivative; and
(b) a pharmaceutical formulation of one or more chemotherapeutic agents for simultaneous, concurrent, separate or sequential use.

The combination partners (a) and (b) can be administered together, one after the other or separately in one combined unit dosage form or in two separate unit dosage forms. The unit dosage form may also be a fixed combination.

BACKGROUND OF THE INVENTION

Camptothecin and derivatives thereof are cytotoxic agents, which exhibit antitumor activity primarily by inhibiting topoisomerase I, a clinically validated drug target which is usually overexpressed in malignant cells. Camptothecin and its derivatives act by interfering with the unwinding of supercoiled DNA by the cellular enzyme topoisomerase I which triggers events leading to apoptosis and programmed death in malignant cells.

SUMMARY OF THE INVENTION

It has now been found that surprisingly camptothecin derivatives are even more efficacious when used in combination with other chemotherapeutic agents. There are both synergistic and additive advantages, both for efficacy and safety. Therapeutic effects of combinations of chemotherapeutic agents with a camptothecin derivative can result in lower safe dosages ranges of each component in the combination.

The invention relates to a method of preventing or treating proliferative diseases or diseases that are associated with or triggered by persistent angiogenesis in a mammal, particularly a human, with a combination of pharmaceutical agents which comprises:

(a) a camptothecin derivative; and
(b) one or more chemotherapeutic agents.

The invention further relates to pharmaceutical compositions comprising:

(a) a camptothecin derivative;
(b) one or more chemotherapeutic agents; and
(c) a pharmaceutically acceptable carrier.

The present invention further relates to a commercial package or product comprising:

(a) a pharmaceutical formulation of a camptothecin derivative; and
(b) a pharmaceutical formulation of one or more chemotherapeutic agents for simultaneous, concurrent, separate or sequential use.

The Chemotherapeutic Agents

The term "chemotherapeutic agents" is a broad one covering many chemotherapeutic agents having different mechanisms of action. Combinations of some of these with camptothecin derivatives can result in improvements in cancer therapy. Generally, chemotherapeutic agents are classified according to the mechanism of action. Many of the available agents are anti-metabolites of development pathways of various tumors, or react with the DNA of the tumor cells.

By the term "chemotherapeutic agent" is meant especially any chemotherapeutic agent other than a topoisomerase I inhibitor or a derivative thereof. It includes, but is not limited to one or more of the following:

i. a microtubule active agent;
ii. an alkylating agent;
iii. an anti-neoplastic anti-metabolite;
iv. a platin compound;
v. topoisomerase II inhibitor;
vi. a compound targeting/decreasing a protein or lipid kinase activity or a protein or lipid phosphatase activity;
vii. monoclonal antibodies;
viii. proteasome inhibitors;
ix. HDAC inhibitors; and
x. tumor cell damaging approaches, such as ionizing radiation.

The term "microtubule active agent", as used herein, relates to microtubule stabilizing, microtubule destabilizing agents and microtublin polymerization inhibitors including, but not limited to, taxanes, e.g., paciltaxel and docetaxel; vinca alkaloids, e.g., vinblastine, especially vinblastine sulfate; vincristine, especially vincristine sulfate and vinorelbine; discodermolides; cochicine and epothilones and derivatives thereof, e.g., epothilone B or a derivative thereof. Paclitaxel is marketed as TAXOL; docetaxel as TAXOTERE; vinblastine sulfate as VINBLASTIN R.P; and vincristine sulfate as FARMISTIN. Also included are the generic forms of paclitaxel, as well as various dosage forms of paclitaxel. Generic forms of paclitaxel include, but are not limited to, betaxolol hydrochloride. Various dosage forms of paclitaxel include, but are not limited to albumin nanoparticle paclitaxel marketed as ABRAXANE; ONXOL, CYTOTAX. Discodermolide can be obtained, e.g., as disclosed in U.S. Pat. No. 5,010,099. Also included are Epotholine derivatives which are disclosed in U.S. Pat. No. 6,194,181, WO 98/10121, WO 98/25929, WO 98/08849, WO 99/43653, WO 98/22461 and WO 00/31247. Especially preferred are epotholine A and/or B.

The term "alkylating agent", as used herein, includes, but is not limited to, cyclophosphamide, ifosfamide, melphalan or nitrosourea (BCNU or Gliadel), or temozolamide (TEMODAR). Cyclophosphamide can be administered, e.g., in the form as it is marketed, e.g., under the trademark CYCLOSTIN; and ifosfamide as HOLOXAN.

The term "anti-neoplastic anti-metabolite" includes, but is not limited to, 5-fluorouracil (5-FU); capecitabine; gemcitabine; DNA de-methylating agents, such as 5-azacytidine and decitabine; methotrexate; edatrexate; and folic acid antagonists, such as, but not limited to, pemetrexed. Capecitabine can be administered, e.g., in the form as it is marketed, e.g., under the trademark XELODA; and gemcitabine as GEMZAR.

The term "platin compound", as used herein, includes, but is not limited to, carboplatin, cisplatin, cisplatinum, oxaliplatin, satraplatin and platinum agents, such as ZD0473. Carboplatin can be administered, e.g., in the form as it is marketed, e.g., CARBOPLAT; and oxaliplatin as ELOXATIN.

The term "topoisomerase II inhibitor", as used herein, includes, but is not limited to, the anthracyclines, such as doxorubicin, including liposomal formulation, e.g., CAELYX; daunorubicin, including liposomal formulation, e.g., DAUNOSOME; epirubicin; idarubicin and nemorubicin; the anthraquinones mitoxantrone and losoxantrone; and the podophillotoxines etoposide and teniposide. Etoposide is marketed as ETOPOPHOS; teniposide as VM 26-BRISTOL; doxorubicin as ADRIBLASTIN or ADRIAMYCIN; epirubicin as FARMORUBICIN; idarubicin as ZAVEDOS; and mitoxantrone as NOVANTRON.

The term "compounds targeting/decreasing a protein or lipid kinase activity; or a protein or lipid phosphatase activity; or further anti-angiogenic compounds", as used herein, includes, but is not limited to, protein tyrosine kinase and/or serine and/or theroine kinase inhibitors or lipid kinase inhibitors, e.g., i. compounds targeting, decreasing or inhibiting the activity of the vascular endothelial growth factor (VEGF) receptors, such as compounds which target, decrease or inhibit the activity of VEGF, especially compounds which inhibit the VEGF receptor, such as, but not limited to, 7H-pyrrolo[2,3-d]pyrimidine derivative; BAY 43-9006; isolcholine compounds disclosed in WO 00/09495, such as (4-tert-butyl-phenyl)-94-pyridin-4-ylmethyl-isoquinolin-1-yl)-amine;

ii. compounds targeting, decreasing or inhibiting the activity of the platelet-derived growth factor (PDGF) receptors, such as compounds which target, decrease or inhibit the activity of PDGF receptors, especially compounds which inhibit the PDGF receptor, e.g., a N-phenyl-2-pyrimidine-amine derivative, e.g., imatinib, SU101, SU6668 and GFB-111;

iii. compounds targeting, decreasing or inhibiting the activity of the fibroblast growth factor (FGF) receptors;

iv. compounds targeting, decreasing or inhibiting the activity of the insulin-like growth factor receptor 1 (IGF-1R), such as compounds which target, decrease or inhibit the activity of IGF-IR, especially compounds which inhibit the IGF-1R receptor. Compounds include, but are not limited to, the compounds disclosed in WO 02/092599 and derivatives thereof of 4-amino-5-phenyl-7-cyclobutyl-pyrrolo[2,3-d]pyrimidine derivatives;

v. compounds targeting, decreasing or inhibiting the activity of the Trk receptor tyrosine kinase family;

vi. compounds targeting, decreasing or inhibiting the activity of the Axl receptor tyrosine kinase family;

vii. compounds targeting, decreasing or inhibiting the activity of the c-Met receptor;

viii. compounds targeting, decreasing or inhibiting the activity of the Ret receptor tyrosine kinase;

ix. compounds targeting, decreasing or inhibiting the activity of the Kit/SCFR receptor tyrosine kinase;

x. compounds targeting, decreasing or inhibiting the activity of the C-kit receptor tyrosine kinases (part of the PDGFR family), such as compounds which target, decrease or inhibit the activity of the c-Kit receptor tyrosine kinase family, especially compounds which inhibit the c-Kit receptor, e.g., imatinib;

xi. compounds targeting, decreasing or inhibiting the activity of members of the c-Abl family and their gene-fusion products, e.g., BCR-Abl kinase, such as compounds which target decrease or inhibit the activity of c-Abl family members and their gene fusion products, e.g., a N-phenyl-2-pyrimidine-amine derivative, e.g., imatinib, PD180970, AG957, NSC 680410 or PD173955 from ParkeDavis; or BMS354825;

xii. compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g., midostaurin; examples of further compounds include, e.g., UCN-01; safingol; BAY 43-9006; Bryostatin 1; Perifosine; Ilmofosine; RO 318220 and RO 320432; GO 6976; Isis 3521; LY333531/LY379196; isochinoline compounds, such as those disclosed in WO 00/09495; FTIs; PD184352 or QAN697, a P13K inhibitor;

xiii. compounds targeting, decreasing or inhibiting the activity of protein-tyrosine kinase, such as imatinib mesylate (GLEEVEC); tyrphostin or pyrymidylaminobenzamide and derivatives thereof. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44(+)enantiomer, Tyrphostin AG 555, AG 494, Tyrphostin AG 556; AG957; and adaphostin (4-{[(2,5-dihydroxyphenyl)methyl]amino}-benzoic acid adamantyl ester; NSC 680410, adaphostin);

xiv. compounds targeting, decreasing or inhibiting the activity of the epidermal growth factor family of receptor tyrosine kinases (EGFR, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF-related ligands, and are in particular those compounds, proteins or monoclonal antibodies generically and specifically disclosed in WO 97/02266, e.g., the compound of Example 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347, e.g., compound known as CP 358774, WO 96/33980, e.g., compound ZD 1839; and WO 95/03283, e.g., compound ZM105180, e.g., trastuzumab (HERCEPTIN), cetuximab, Iressa, OSI-774, CI-1033, EKB-569, GW-2016, E1.1, E2.4, E2.5, E6.2, E6.4, E2.11, E6.3 or E7.6.3, and {6-[4-(4-ethyl-piperazin-1-ylmethyl)-phenyl]-7H-pyrrolo[2,3-d]pyrimidin-4-yl]-((R)-1-phenyl-ethyl)-amine, erlotinib and gefitinib. Erlotinib can be administered in the form as it is marketed, e.g., TARCEVA, and gefitinib as IRESSA, human monoclonal antibodies against the epidermal growth factor receptor including ABX-EGFR; and xv. compounds which target, decrease or inhibit the activity/function of serine/threonine mTOR kinase are especially compounds, proteins or antibodies which target/inhibit members of the mTOR kinase family, e.g., RAD, RAD001, CCI-779, ABT578, SAR543, rapamycin and derivatives/analogs thereof, AP23573 and AP23841 from Ariad, everolimus (CERTICAN) and sirolimus. CERTICAN (everolimus, RAD) an investigational novel proliferation signal inhibitor that prevents proliferation of T-cells and vascular smooth muscle cells.

The term "monoclonal antibodies", as used herein, includes, but is not limited to bevacizumab, cetuximab, trastuzumab, Ibritumomab tiuxetan, and tositumomab and iodine 1131. Bevacizumab can be administered in the form as it is marketed, e.g., AVASTIN; cetuximab as ERBITUX; trastuzumab as HERCEPTIN; rituximab as MABTHERA; ibritumomab tiuxetan as ZEVULIN; and tositumomab and iodine 1131 as BEXXAR.

The term "proteasome inhibitors", as used herein, includes compounds which target, decrease or inhibit the activity of the proteosome. Compounds which target, decrease or inhibit the activity of the proteosome include, but are not limited to, PS-341; MLN 341, bortezomib or velcade.

The term "HDAC inhibitor", as used herein, relates to relates to compounds which inhibit the histone deacetylase and which possess anti-proliferative activity. This includes but is not limited to compounds disclosed in WO 02/22577, especially N-hydroxy-3-[4-[[(2-hydroxyethyl)[2-(1H-indol-3-yl)ethyl]-amino]methyl]phenyl]-2E-2-propenamide; and N-hydroxy-3-[4-[[[2-methyl-1H-indol-3-yl)-ethyl]-amino]methyl]phenyl]-2E-2-propenamide; and pharmaceutically acceptable salts thereof. It further especially includes suberoylanilide hydroxamic acid (SAHA); [4-(2-amino-phenylcarbamoyl)-benzyl]-carbamic acid pyridine-3-ylmethyl ester and derivatives thereof; butyric acid, pyroxamide, trichostatin A, oxamflatin, apicidin, depsipeptide, depudecin and trapoxin.

"Tumor cell damaging approaches" refers to approaches, such as ionizing radiation. The term "ionizing radiation", referred to above and hereinafter, means ionizing radiation that occurs as either electromagnetic rays, such as X-rays and gamma rays; or particles, such as alpha, beta and gamma particles. Ionizing radiation is provided in, but not limited to, radiation therapy and is known in the art. See Hellman, Cancer, 4$^{th}$ Edition, Vol. 1, Devita et al., Eds., pp. 248-275 (1993).

In each case where citations of patent applications or scientific publications are given, in particular with regard to the respective compound claims and the final products of the working examples therein, the subject matter of the final products, the pharmaceutical preparations and the claims is hereby incorporated into the present application by reference to these publications. Comprised are likewise the corresponding stereoisomers, as well as the corresponding crystal modifications, e.g., solvates and polymorphs, which are disclosed therein. The compounds used as active ingredients in the combinations disclosed herein can be prepared and administered as described in the cited documents, respectively.

The structure of the active agents identified by code numbers, generic or trade names may be taken from the actual edition of the standard compendium "The Merck Index" or from databases, e.g., Patents International, e.g., IMS World Publications, or the publications mentioned above and below. The corresponding content thereof is hereby incorporated by reference.

It will be understood that references to the components (a) and (b) are meant to also include the pharmaceutically acceptable salts of any of the active substances. If active substances comprised by components (a) and/or (b) have, e.g., at least one basic center, they can form acid addition salts. Corresponding acid addition salts can also be formed having, if desired, an additionally present basic center. Active substances having an acid group, e.g., COOH, can form salts with bases. The active substances comprised in components (a) and/or (b) or a pharmaceutically acceptable salts thereof may also be used in form of a hydrate or include other solvents used for crystallization. 7-t-Butoxyiminomethyl-camptothecin is the most preferred combination partner (a).

The camptothecin derivatives for use in the present invention include those disclosed in U.S. Pat. No. 6,242,457, incorporated herein by reference, and have the following formula (I):

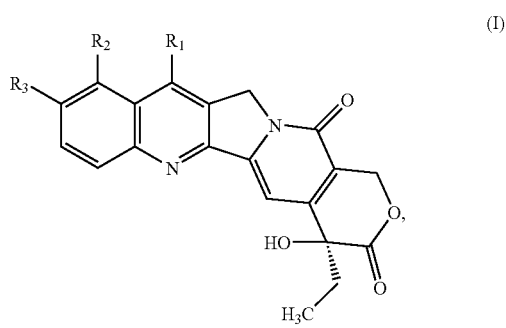

wherein
R$_1$ is a —C(R$_5$)=N—O(n)R$_4$ group,
wherein
R$_4$ is hydrogen or a C$_1$-C$_8$ linear or branched alkyl or C$_1$-C$_8$ linear or branched alkenyl group or C$_3$-C$_{10}$ cycloalkyl, or C$_3$-C$_{10}$ cycloalkylC$_1$-C$_8$ linear or branched alkyl group, or C$_6$-C$_{14}$ aryl, or C$_6$-C$_{14}$ aryl C$_1$-C$_8$ linear or branched alkyl group, or a heterocyclic or heterocyclo C$_1$-C$_8$ linear or branched alkyl group, said heterocyclic group containing at least a heteroatom selected from the group consisting of nitrogen atom, optionally substituted with a C$_1$-C$_8$ alkyl group, and/or oxygen and/or sulfur; said alkyl, alkenyl, cycloalkyl, cycloalkylalkyl, aryl, aryl-alkyl, heterocyclic or heterocyclo alkyl groups, being optionally substituted with one or more groups selected from the group consisting of: halogen, hydroxyl, keto, C$_1$-C$_8$ alkyl, C$_1$-C$_8$ alkoxy, phenyl, cyano, nitro, —NR$_6$R$_7$, wherein R$_6$ and R$_7$, the same or different between them, are hydrogen, C$_1$-C$_8$ linear or branched alkyl; the —COOH group or a pharmaceutically acceptable ester thereof, or the —CONR$_8$R$_9$ group, wherein R$_8$ and R$_9$, the same or different between them, are hydrogen, C$_1$-C$_8$ linear or branched alkyl; phenyl, or
R$_4$ is a C$_6$-C$_{10}$ aroyl or C$_6$-C$_{10}$ arylsulfonyl group, optionally substituted with one or more groups selected from the group consisting of: halogen, hydroxy, C$_1$-C$_8$ linear or branched alkyl, C$_1$-C$_8$ linear or branched alkoxy, phenyl, cyano, nitro, —NR$_{10}$R$_{11}$, wherein R$_{10}$ and R$_{11}$, the same or different between them are hydrogen, C$_1$-C$_8$ linear or branched alkyl, or
R$_4$ is a polyaminoalkyl group;
n is the number 1;
R$_5$ is hydrogen, C$_1$-C$_8$ linear or branched alkyl, C$_1$-C$_8$ linear or branched alkenyl, C$_3$-C$_{10}$ cycloalkyl, C$_3$-C$_{10}$ cycloalkyl C$_1$-C$_8$ linear or branched alkyl, C$_6$-C$_{14}$ aryl, C$_6$-C$_{14}$ aryl C$_1$-C$_8$ linear or branched alkyl;
R$_2$ and R$_3$, the same or different between them are hydrogen, hydroxy, C$_1$-C$_8$ linear or branched alkoxy; and
their N$_1$-oxides, their single isomers, their possible enantiomers, diastereoisomers and relative admixtures, the pharmaceutically acceptable salts thereof and their active metabolites; with the proviso that when $R_5$, $R_2$ and $R_3$ are hydrogen, then $R_4$ is different from hydrogen.

Within the scope of the present invention, as examples of $C_1$-$C_8$ linear or branched alkyl group, methyl, ethyl, propyl, butyl, pentyl and acetyl are meant and their possible isomers, such as, e.g., isopropyl, isobutyl or tert-butyl.

Examples of $C_1$-$C_8$ linear or branched alkenyl group are methylene, ethylidene, vinyl, allyl, proparyl, butylenes, pentylene, wherein the carbon-carbon double bond, optionally in the presence of other carbon-carbon unsaturations, can be situation in the different possible positions of the alkyl chain, which can also be branched with the allowed isomery.

Examples of $C_3$-$C_{10}$ cycloalkyl group are cyclopropyl, cyclobutyl, cyclopentyl, cyclohexyl, cycloctyl and polycyclic groups, such as, e.g., adamantyl.

Examples of $C_3$-$C_{10}$ cycloalkyl $C_1$-$C_8$ linear or branched alkyl group are cyclopropylmethyl, 2-cyclopropylethyl, 1-cyclopropylethyl, 3-cyclopropylpropyl, 2-cyclopropylpropyl, 1-cyclopropylpropyl, cyclobutylmethyl, 2-cyclobutylethyl, 1-cyclobutylethyl, 3-cyclobutylpropyl, 2-cyclobutylpropyl, 1-cyclobutylpropyl, cyclohexylmethyl, 2-cyclohexylethyl, 1-cyclohenxylethyl, 3-cyclohexylpropyl, 2-cyclohexylpropyl, 1-cyclohexylpropyl, 5-cyclohexylpentyl, 3-cyclohexylpentyl, 3-methyl-2-cyclohexylbutyl, 1-adamantylethyl, 2-adamantylethyl and adamantylmethyl.

Examples of $C_6$-$C_{14}$ aryl, or $C_6$-$C_{14}$ aryl $C_1$-$C_8$ linear or branched alkyl group are phenyl, 1- or 2-naphthyl, anthryl, benzyl, 2-phenylethyl, 1-phenylethyl, 3-phenylpropyl, 2-anthrylpropyl, 1-anthrylpropyl, naphthylmethyl, 2-naphthylethyl, 1-naphthylethyl, 3-napthylpropyl, 2-napthylpropyl, 1-napthylpropyl, cyclohexylmethyl, 5-phenylpentyl, 3-phenylpentyl and 2-phenyl-3-methylbutyl.

Examples of heterocyclic- or heterocyclo $C_1$-$C_8$ linear or branched alkyl group are thienyl, quinolyl, pyridyl, N-methylpyperidinyl, 5-tetrazolyl, 2-(4,5-dihydroxazolyl)1,2,4-oxadiazolidin-3-yl-5-one, purine and pyrimidine bases, e.g., uracyl, optionally substituted as shown in the general definitions above mentioned.

Examples of $C_6$-$C_{10}$ aroyl groups are benzoyl and naphthoyl.

Examples of $C_6$-$C_{10}$ arylsulfonyl groups, optionally substituted with an alkyl group, are tosyl and benzenesulfonyl. As halogen, it is intended fluorine, chlorine, bromine and iodine.

Examples of substituted groups are pentafluorophenyl, 4-phenylbenzyl, 2,4-difluorobenzyl, 4-aminobutyl, 4-hydroxybutyl, dimethylaminoethyl and p-nitrobenzoyl, p-cyanobenzoyl.

Examples of polyaminoalkyl group is —$(CH_2)_m$—$NR_{12}$—$(CH_2)_p$—$NR_{13}$—$(CH_2)_q$—$NH_2$,
wherein
m and p are an integer from 2-6;
q is an integer from 0-6, extremes included; and
$R_{12}$ and $R_{13}$ are a $C_1$-$C_8$ linear or branched alkyl group, e.g., N-(4-aminobutyl)2-aminoethyl, N-(3-aminopropyl)-4-aminobutyl and N-[N-(3-aminopropyl)-N-(4-aminobutyl)]-3-aminopropyl.

Examples of glycosyl groups are 6-D-galactosyl, 6-D-glucosyl, D-galactopyranosyl, the glycosyl group being optionally protected with a suitable ketal group, isopropylidene, for instance.

Examples of pharmaceutically acceptable salts are, in case of nitrogen atoms having basic character, the salts with pharmaceutically acceptable acids, both inorganic and organic, such as, e.g., hydrochloric acid, sulfuric acid and acetic acid; or in the case of acid group, such as carboxyl; the salts with pharmaceutically acceptable bases, both inorganic and organic, such as, e.g., alkaline and alkaline-earth hydroxides; ammonium hydroxide; amine; and also heterocyclic ones.

$R_1$ is preferably —C($R_5$)═N—O$_{(n)}$$R_4$, wherein $R_4$ is preferably a $C_1$-$C_8$ linear or branched alkyl; and $R_2$ and $R_3$ are preferably hydrogen.

High preference is given to a compound selected from the group consisting of:

7-methyoxyiminomethylcamptothecin;
7-methoxyiminomethyl-10-hydroxycamptothecin;
7-(tert-butoxycarbonyl-2-propoxy)iminomethylcamptothecin;
7-ethoxyiminomethylcamptothecin;
7-isopropoxyiminomethylcamptothecin;
7-(2-methylbutoxy)iminomethylcamptothecin;
7-t-butoxyiminomethylcamptothecin;
7-t-butoxyiminomethyl-10-hydroxycamptothecin;
7-t-butoxyiminomethyl-10-methoxycamptothecin;
7-(4-hydroxybutoxy)iminomethylcamptothecin;
7-triphenylmethoxyiminomethylcamptothecin;
7-carboxymethoxyiminomethylcamptothecin;
7-(2-amino)ethoxyiminomethylcamptothecin;
7-(2-N,N-dimethylamino)ethoxyiminomethylcamptothecin;
7-allyloxyiminomethylcamptothecin;
7-cyclohexyloxyiminoethylcamptothecin;
7-cyclohexylmethoxyiminomethylcamptothecin;
7-cyclooctyloxyiminomethylcamptothecin;
7-cyclooctylmethoxyiminomethylcamptothecin;
7-benzyloxyiminomethylcamptothecin;
7-[(1-benzyloxyimino)-2-phenylethyl]camptothecin;
7-(1-benzyloxyimino)ethylcamptothecin;
7-phenoxyiminomethylcamptothecin;
7-(1-t-butoxyimino)ethylcamptothecin;
7-p-nitrobenzyloxyiminomethylcamptothecin;
7-p-methylbenzyloxyiminomethylcamptothecin;
7-pentafluorobenzyloxyiminomethylcamptothecin;
7-p-phenylbenzyloxyiminomethylcamptothecin;
7-[2-(2,4-difluorophenyl)ethoxy]iminomethylcamptothecin;
7-(4-t-butylbenzyloxy)iminomethylcamptothecin;
7-(1-adamantyloxy)iminomethylcamptothecin;
7-(1-adamantylmethoxy)iminomethylcamptothecin;
7-(2-naphthyloxy)iminomethylcamptothecin;
7-(9-anthrylmethoxy)iminomethylcamptothecin;
7-oxiranylmethoxyiminomethylcamptothecin;
7-(6-uracyl)methoxyiminomethylcamptothecin;
7-[2-(1-urcyl)ethoxy]iminomethylcamptothecin;
7-(4-pyridyl)methoxyiminomethylcamptothecin;
7-(2-thienyl)methoxyiminomethylcamptothecin;
7-[(N-methyl)-4-piperidinyl]methoxyiminomethylcamptothecin;
7-[2-(4-morholininyl]ethoxy]iminomethylcamptothecin;
7-(benzoyloxyiminomethyl)camptothecin;
7-[(1-hydroxyimino)-2-phenylethyl)camptothecin;
7-tert-butyloxyiminomethylcamptothecin-N-oxide; and
7-methoxyiminomethylcamptothecin-N-oxide.

In a very preferred embodiment of the invention, the camptothecin derivative of formula (I) has the following structure:

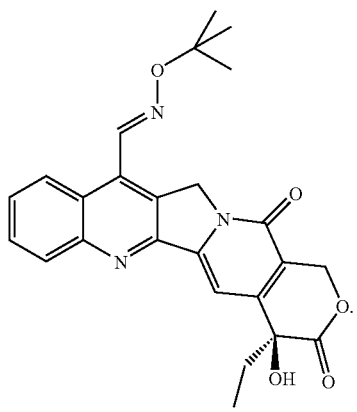 [SMILES: CC[C@@]1(O)C(=O)OCc2c1cc1n(c2=O)Cc2c-1nc1ccccc1c2/C=N/OC(C)(C)C]

Camptothecin derivatives of formula (I) and their preparation are disclosed in U.S. Pat. No. 6,242,457, which is incorporated herein in its entirety.

The Combinations

Thus, in a first aspect, the present invention relates to a method for the prevention of treatment of proliferative diseases or diseases that are triggered by persistent angiogenesis in a mammal, preferably a human patient, which comprises treating the patient concurrently or sequentially with pharmaceutically effective amounts of a combination of:
(a) a camptothecin derivative, preferably of formula (I); and
(b) one or more chemotherapeutic agents.

In another aspect, the present invention relates to a pharmaceutical composition comprising a combination of:
(a) a camptothecin derivative, preferably of formula (I); and
(b) one or more chemotherapeutic agents.

In a yet further aspect, the present invention provides a pharmaceutical preparation comprising:
(a) a camptothecin derivative of formula (I); and
(b) one or more chemotherapeutic agents, together with a pharmaceutically acceptable carrier.

In preferred embodiment, the present invention provides a pharmaceutical preparation comprising:
(a) a camptothecin derivative of formula (I); and
(b) one or more chemotherapeutic agents selected from a microtubule active agent; an alkylating agent; an anti-neoplastic anti-metabolite; a platin compound; a topoisomerase II inhibitor; a VEGF inhibitor; a tyrosine kinase inhibitor; an EGFR kinase inhibitor; an mTOR kinase inhibitor; an insulin-like growth factor I inhibitor; a Raf kinase inhibitor; a monoclonal antibody; a proteasome inhibitor; a HDAC inhibitor; and ionizing radiation.

In another preferred embodiment, the present invention provides a pharmaceutical preparation comprising:
(a) a camptothecin derivative of formula (I); and
(b) one or more chemotherapeutic agents selected from paclitaxel; docetaxel; epothilone B; temozolamide; 5-FU; gemcitabine; oxaliplatin; cisplatinum; carboplatin; doxorubicin; {6-[4-(4-ethyl-piperazin-1-ylmethyl)-phenyl]-7H-pyrrolo[2,3-d]pyrimidin-4-yl]-((R)-1-phenyl-ethyl)-amine; everolimus; imatinib; erlotinib, bevacizumab, cetuximab, and velcade;

Any of the combination of components (a) and (b), the method of treating a warm-blooded animal comprising administering these two components, a pharmaceutical composition comprising these two components for simultaneous, separate or sequential use, the use of the combination for the delay of progression or the treatment of a proliferative disease or for the manufacture of a pharmaceutical preparation for these purposes or a commercial product comprising such a combination of components (a) and (b), all as mentioned or defined above, will be referred to subsequently also as COMBINATION OF THE INVENTION (so that this term refers to each of these embodiments which thus can replace this term where appropriate).

Simultaneous administration may, e.g., take place in the form of one fixed combination with two or more active ingredients, or by simultaneously administering two or more active ingredients that are formulated independently. Sequential use (administration) preferably means administration of one (or more) components of a combination at one time point, other components at a different time point, that is, in a chronically staggered manner, preferably such that the combination shows more efficiency than the single compounds administered independently (especially showing synergism). Separate use (administration) preferably means administration of the components of the combination independently of each other at different time points.

Also combinations of two or more of sequential, separate and simultaneous administration are possible, preferably such that the combination component-drugs show a joint therapeutic effect that exceeds the effect found when the combination component-drugs are used independently at time intervals so large that no mutual effect on their therapeutic efficiency can be found, a synergistic effect being especially preferred.

The term "delay of progression", as used herein, means administration of the combination to patients being in a pre-stage or in an early phase, of the first or subsequent manifestations; or a relapse of the disease to be treated in which patients, e.g., a pre-form of the corresponding disease is diagnosed; or which patients are in a condition, e.g., during a medical treatment or a condition resulting from an accident, under which it is likely that a corresponding disease will develop.

"Jointly therapeutically active" or "joint therapeutic effect" means that the compounds may be given separately (in a chronically staggered manner, especially a sequence-specific manner) in such time intervals that they preferably, in the warm-blooded animal, especially human, to be treated, still show a (preferably synergistic) interaction (joint therapeutic effect).

"Pharmaceutically effective" preferably relates to an amount that is therapeutically or in a broader sense also prophylactically effective against the progression of a proliferative disease.

The term "a commercial package" or "a product", as used herein defines especially a "kit of parts" in the sense that the components (a), which is the camptothecin derivative and (b), which includes one or more chemotherapeutic agents, as defined above, can be dosed independently or by use of different fixed combinations with distinguished amounts of the components (a) and (b), i.e., simultaneously or at different time points. Moreover, these terms comprise a commercial package comprising (especially combining) as active ingredients components (a) and (b), together with instructions for simultaneous, sequential (chronically staggered, in time-specific sequence, preferentially) or (less preferably) separate use thereof in the delay of progression or treatment of a proliferative disease. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b) as can be determined according to standard methods. The ratio of the total amounts of the combination partner (a) to the combination partner (b) to be administered in the combined preparation can be varied, e.g., in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular, a more than additive effect, which hence could be achieved with lower doses of each of the combined drugs, respectively, than tolerable in the case of treatment with the individual drugs only without combination, producing additional advantageous effects, e.g., less side effects or a combined therapeutic effect in a non-effective dosage of one or both of the combination partners (components) (a) and (b), and very preferably a strong synergism of the combination partners (a) and (b).

Both in the case of the use of the combination of components (a) and (b) and of the commercial package, any combination of simultaneous, sequential and separate use is also possible, meaning that the components (a) and (b) may be administered at one time point simultaneously, followed by administration of only one component with lower host toxicity either chronically, e.g., more than 3-4 weeks of daily dosing, at a later time point and subsequently the other component or the combination of both components at a still later time point (in subsequent drug combination treatment courses for an optimal anti-tumor effect) or the like.

The COMBINATION OF THE INVENTION can also be applied in combination with other treatments, e.g., surgical intervention, hyperthermia and/or irradiation therapy.

The pharmaceutical compositions according to the present invention can be prepared by conventional means and are those suitable for enteral, such as oral or rectal, and parenteral administration to mammals including man, comprising a therapeutically effective amount of a camptothecin derivative and at least one chemotherapeutic agent alone or in combination with one or more pharmaceutically acceptable carriers, especially those suitable for enteral or parenteral application.

The pharmaceutical compositions comprise from about 0.00002% to about 100%, especially, e.g., in the case of infusion dilutions that are ready for use) of 0.0001-0.02%, or, e.g., in case of injection or infusion concentrates or especially parenteral formulations, from about 0.1% to about 95%, preferably from about 1% to about 90%, more preferably from about 20% to about 60%, active ingredient (weight by weight, in each case). Pharmaceutical compositions according to the invention may be, e.g., in unit dose form, such as in the form of ampoules, vials, dragées, tablets, infusion bags or capsules.

The effective dosage of each of the combination partners employed in a formulation of the present invention may vary depending on the particular compound or pharmaceutical compositions employed, the mode of administration, the condition being treated and the severity of the condition being treated. A physician, clinician or veterinarian of ordinary skill can readily determine the effective amount of each of the active ingredients necessary to prevent, treat or inhibit the progress of the condition.

In the instance where the chemotherapeutic agent is selected from the group consisting of doxorubicin, paclitaxel, docetaxel, epothilones and derivatives thereof, temozolamide, 5-FU; gemcitabine, oxaliplatin, carboplatin, 7H-pyrrol-[2,3-d]pyrimidine derivatives, isochinoline compounds, RAD001, GLEEVEC, erlotinib, bevacizumab, cetuximab, velcade, N-hydroxy-3-[4-[[(2-hydroxy-ethyl)[2-(1H-indol-3-yl)ethyl]-amino]methyl]phenyl]-2E-2-propenamide and 4-amino-5-phenyl-7-cyclobutyl-pyrrolo[2,3-d]pyrimidine derivatives pharmaceutically acceptable salts or solvates thereof; and pharmaceutically acceptable prodrug esters thereof; and the patient to be treated is a human, an appropriate dose of, e.g., 5-FU is administered at an appropriate dose in the range from 100-1500 mg daily, e.g., 200-1000 mg/day, such as 200, 400, 500, 600, 800, 900 or 1000 mg/day, administered in one or two doses daily. 5-FU may be administered to a human in a dosage range varying from about 50-1000 mg/m$^2$/day, e.g., 500 mg/m$^2$/day. Among the topoisomerase II inhibitors, DOXORUBICIN may be administered to a human in a dosage range varying from about 10-100 mg/m$^2$/day, e.g., 25 or 75 mg/m$^2$/day, e.g., as single dose. PACLITAXEL may be administered to a human in a dosage range varying from about 50-300 mg/m$^2$ day. DOCETAXEL may be administered to a human in a dosage range varying from about 25-100 mg/m$^2$/day. CARBOPLATIN may be administered to a human in a dosage range varying from about 200-400 mg/m$^2$ about every four weeks. OXALIPLATIN may be administered to a human in a dosage range varying from about 50-85 mg/m$^2$ every two weeks.

Pharmaceutical preparations for the combination therapy for enteral or parenteral administration are, e.g., those in unit dosage forms, such as sugar-coated tablets, capsules or suppositories; and furthermore ampoules. If not indicated otherwise, these formulations are prepared by conventional means, e.g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units. One of skill in the art has the ability to determine appropriate pharmaceutically effective amounts of the combination components.

Preferably, the compounds or the pharmaceutically acceptable salts thereof, are administered as an oral pharmaceutical formulation in the form of a tablet, capsule or syrup; or as parenteral injections if appropriate.

In preparing compositions for oral administration, any pharmaceutically acceptable media may be employed, such as water, glycols, oils, alcohols, flavoring agents, preservatives or coloring agents. Pharmaceutically acceptable carriers include starches, sugars, microcrystalline celluloses, diluents, granulating agents, lubricants, binders and disintegrating agents.

Solutions of the active ingredient, and also suspensions, and especially isotonic aqueous solutions or suspensions, are useful for parenteral administration of the active ingredient, it being possible, e.g., in the case of lyophilized compositions that comprise the active ingredient alone or together with a pharmaceutically acceptable carrier, e.g., mannitol, for such solutions or suspensions to be produced prior to use. The pharmaceutical compositions may be sterilized and/or may comprise excipients, e.g., preservatives, stabilizers, wetting and/or emulsifying agents, solubilizers, salts for regulating the osmotic pressure and/or buffers, and are prepared in a manner known per se, e.g., by means of conventional dissolving or lyophilizing processes. The solutions or suspensions may comprise viscosity-increasing substances, such as sodium carboxymethylcellulose, carboxymethylcellulose, dextran, polyvinylpyrrolidone or gelatin. Suspensions in oil comprise as the oil component the vegetable, synthetic or semi-synthetic oils customary for injection purposes.

The isotonic agent may be selected from any of those known in the art, e.g., mannitol, dextrose, glucose and sodium chloride. The infusion formulation may be diluted with the aqueous medium. The amount of aqueous medium employed as a diluent is chosen according to the desired concentration of active ingredient in the infusion solution. Infusion solutions may contain other excipients commonly employed in formulations to be administered intravenously, such as antioxidants.

The present invention further relates to "a combined preparation", which, as used herein, defines especially a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit of parts can then, e.g., be administered simultaneously or chronologically staggered, that is at different time points and with equal or different time intervals for any part of the kit of parts. The ratio of the total amounts of the combination partner (a) to the combination partner (b) to be administered in the combined preparation can be varied, e.g., in order to cope with the needs of a patient sub-population to be treated or the needs of the single patient based on the severity of any side effects that the patient experiences.

The present invention especially relates to a combined preparation which comprises:
(a) one or more unit dosage forms of a camptothecin derivative; and
(b) one or more unit dosage forms of an chemotherapeutic agent.

The Diseases to be Treated

The compositions of the present invention are useful for treating proliferative diseases or diseases that are associated with or triggered by persistent angiogenesis.

A proliferative disease is mainly a tumor disease (or cancer) (and/or any metastases). The inventive compositions are particularly useful for treating a tumor which is a breast cancer; lung cancer, including non-small cell lung cancer (NSCLC) and small-cell lung cancer (SCLC); gastrointestinal cancer, including esophageal, gastric, small bowel, large bowel, rectal and colon cancer; glioma, including glioblastoma; sarcoma, such as those involving bone, cartilage, soft tissue, muscle, blood and lymph vessels; ovarian cancer; myeloma; female cervical cancer; endometrial cancer; head and neck cancer; mesothelioma; renal cancer; uteran; bladder and urethral cancers; leukemia; prostate cancer; skin cancers; and melanoma. In particular, the inventive compositions are particularly useful for treating:
  i. a breast tumor; a lung tumor, e.g., non-small cell lung tumor, including non-small cell lung cancer (NSCLC) and small-cell lung cancer (SCLC); a gastrointestinal tumor, e.g., a colorectal tumor; or a genitourinary tumor, e.g., a prostate tumor; ovarian cancer; glioma, including glioblastoma;
  ii. a proliferative disease that is refractory to the treatment with other chemotherapeutics; or
  iii. a tumor that is refractory to treatment with other chemotherapeutics due to multidrug resistance.

In a broader sense of the invention, a proliferative disease may furthermore be a hyperproliferative condition, such as a leukemia, lymphoma or multiple myeloma.

The combination of the present invention can also be used to prevent or treat diseases that are triggered by persistent angiogenesis, such as Kaposi's sarcoma, leukemia or arthritis.

Where a tumor, a tumor disease, a carcinoma or a cancer are mentioned, also metastasis in the original organ or tissue and/or in any other location are implied alternatively or in addition, whatever the location of the tumor and/or metastasis.

The compositions are selectively toxic or more toxic to rapidly proliferating cells than to normal cells, particularly in human cancer cells, e.g., cancerous tumors, the compound has significant anti-proliferative effects and promotes differentiation, e.g., cell cycle arrest and apoptosis.

The invention is further defined by reference to the following examples describing in detail the compounds, compositions and combinations of the present invention, as well as their utility. It will be apparent to those skilled in the art, that many modifications, both to materials, and methods, may be practiced with out departing from the purpose and interest of this invention. The examples that follow are not intended to limit the scope of the invention as defined hereinabove or as claimed below.

EXAMPLE 1

Combination of 7-t-butoxyiminomethylcamptothecin and Oxaliplatin

In Vivo Experimental Procedures
Test system: Female CD1 nu/nu mice for tumor models were used.
Number of animals: 176 (88 for each tumor model)
A2780 tumor model: human ovarian carcinoma cells ($2\times10^6$) are implanted s.c. in the right flank of female mice, 7-8 mice/group are treated 3 days after tumor injection with the following drugs.
  1. Vehicle
  2. 7-t-butoxyiminomethylcamptothecin 0.28 mg/10 ml/kg and 0.19 mg/10 ml/kg, p.o. (qdx5/w, days 3-7)
  3. Oxaliplatin 7 mg/10 ml/kg and 4.7 mg/10 ml/kg, i.p. (q4dx2, days 3, 7).
  4. Combination groups: 7-t-butoxyiminomethylcamptothecin+oxaliplatin: 0.28+7, 0.28+4.7, 0.19+7, 0.19+4.7.
  5. 7-t-butoxyiminomethylcamptothecin 0.19 mg/10 ml/kg, p.o. (qdx5/wx2w, days 3-7, 10-14).
  6. Oxaliplatin 7 mg/10 ml/kg, i.p. (q7dx2, days 3, 10).
  7. Combination groups: 7-t-butoxyiminomethylcamptothecin+oxaliplatin 0.19+7.

The drug is administered 1 h before 7-t-butoxyiminomethylcamptothecin.

Data Analysis

All raw data are recorded on appropriate forms bound in numbered registers, stored and processed by a computer system. The formula TV (mm3)=length (mm)×width (mm)2]/2 is used, where the width and the length are the shortest and the longest diameters of each tumor, respectively. LCK ($\log_{10}$ cell kill) is calculated using the following formula: (T−C)/3.32×DT where T−C are the mean time (in days) required for treated (T) and control (C) tumors, respectively, to reach a determined volume, and DT is the doubling time of control tumors. CR is defined as disappearance of the tumor lasting at least 10 days after the end of treatments. The effect of the combination of 7-t-butoxyiminomethylcamptothecin and the different agents is evaluated according to the method of Romanelli et al. (1998). An R index of 1 (additive effect) or lower indicates the absence of synergism. Synergism is defined as any value of R greater than unity. R was calculated from expected and observed T/C % values.

A2780 ovarian carcinoma: 7-t-butoxyiminomethylcamptothecin at the MTD of 0.28 mg/kg shows a potent antitumor activity in terms of tumor volume inhibition (TVI=100%), CR=8/8 and LCK>2. The combination of 7-t-butoxyiminomethylcamptothecin with oxaliplatin on the same tumor gave activity comparable to 7-t-butoxyiminomethylcamptothecin as single agent but with some complete responders at 60 days.

Antitumor activity of 7-t-butoxyiminomethylcamptothecin [A]
(p.o., qdx5/w, +3) in combination with oxaliplatin [B]
(i.p., q4dx2, +3) against A2780 ovarian carcinoma

| Drug | Dose (mg/kg) | BWL %[1] | Tox[2] | TVI %[3] | CR[4] | LCK[5] |
|---|---|---|---|---|---|---|
| A | 0.19 | 6 | 0/8 | 100 | 8/8 | 2.15 |
| A | 0.28 | 13 | 0/8 | 100 | 8/8 | 2.44 |
| B | 4.7 | 2 | 1/8 | 67 | 1/8 | 0.57 |
| B | 7 | 10 | 0/8 | 91 | 0/8 | 1.0 |
| B + A | 4.7 + 0.19 | 14 | 0/8 | 100 | 8/8 | 2.29 |
| B + A | 4.7 + 0.28 | 22 | 0/8 | 100 | 8/8 | 2.58 |
| B + A | 7 + 0.19 | 24 | 0/8 | 100 | 8/8 | 2.44 |
| B + A | 7 + 0.28 | 31 | 4/8 | 100 | 4/4 | 3.15 |

Treatment starts 3 days after the tumor injection.
[1]Body weight loss % induced by drug treatment.
[2]Dead/treated mice.
[3]Tumor volume inhibition % in treated over control tumors.
[4]CR = complete response after the last treatment.
[5]LCK = log10 cell kill. DT = 2.1 days. On day +60 the following mice were without tumor lesions: 4.7 + 0.19 (1/8), 7 + 0.19 (1/8).

EXAMPLE 2

Combination of 7-t-butoxyiminomethylcamptothecin and Docetaxel

In Vivo Experimental Procedures
Test system: Female CD1 nu/nu mice for tumor models are used.
Number of animals: 176 (88 for each tumor model)
MCF-7 human breast carcinoma estrogen-dependent cells (5×106) are implanted in the right flank of female mice previously implanted with slow-release pellets of 17β-estradiol (0.72 mg/pellet). The pellets are placed in the inter scapular region one day before the tumor cells inoculation. 8 mice/group are treated 6 days after tumor injection with the following drugs:
 1. Vehicle
 2. 7-t-butoxyiminomethylcamptothecin 0.28 mg/10 ml/kg and 0.19 mg/10 ml/kg p.o. (qdx5/w, days 3-7)
 3. Docetaxel 20 mg/10 ml/kg. and 13.3 mg/10 ml/kg i.p. (q3-4dx2, days 3, 7).
 4. Combination groups 7-t-butoxyiminomethylcamptothecin+docetaxel: 0.28+20, 0.28+13.3, 0.19+20, 0.19+13.3.

A2780/DDP human platinum ovarian carcinoma cells (2×106) are implanted in the right flank of female mice. 8 mice/group are treated 3 days after tumor injection with the following drugs.
 1. Vehicle
 2. 7-T-butoxyiminomethylcamptothecin 0.28 mg/10 ml/kg and 0.19 mg/10 ml/kg p.o. (qdx5/w, days 3-7)
 3. Docetaxel 20 mg/10 mi/kg and 13.3 mg/10 ml/kg, i.p. (q4dx2, days 3, 7)
 4. Combination groups 7-t-butoxyiminomethylcamptothecin+docetaxel: 0.28+20, 0.28+13.3, 0.19+20, 0.19+13.3.

NCI-H460 human non-small cell lung carcinoma cells (3×106) are implanted in the right flank of female mice. 8 mice/group are treated 3 days after tumor injection with the following drugs:
 1. Vehicle
 2. 7-t-butoxyiminomethylcamptotheciN 0.28 mg/10 ml/kg and 0.19 mg/10 ml/kg p.o. (qdx5/w, days 3-7)
 3. Docetaxel 20 mg/10 ml/kg and 13.3 mg/10 ml/kg i.p. (q4dx2, days 3, 7)
 4. Combination groups 7-t-butoxyiminomethylcamptothecin+docetaxel: 0.28+20, 0.28+13.3, 0.19+20, 0.19+13.3.

7 mice/group are treated 3 days after tumor injection with the following drugs:
 1. 7-t-butoxyiminomethylcamptothecin 0.19 mg/10 ml/kg, p.o. (qdx5/wx2w, days 3-7, 10-14)
 2. Docetaxel 20 mg/10 ml/kg, i.p. (q7dx2, days 3, 10)

DU145 human prostate carcinoma cells are inoculated (3×106) s.c. into the right flank of male mice. 8 mice/group are treated 14 days after tumor injection with the following drugs:
 1. Vehicle
 2. 7-t-butoxyiminomethylcamptothecin 0.25 mg/10 ml/kg and 0.19 mg/10 ml/kg, p.o. (qdx5/w, days 14-18)
 3. Docetaxel 20 mg/10 ml/kg and 13.3 mg/10 ml/kg, i.p. (q4dx2, days 14-18)
 4. Combination groups 7-t-butoxyiminomethylcamptothecin+docetaxel: 0.19+13.3, 0.25+13.3.

8 mice/group are also treated 14 days after tumor injection with the following drugs:
 1. 7-t-butoxyiminomethylcamptothecin 0.17 mg/10 ml/kg, p.o. (qdx5/wx3w, days 14-18, 21-25, 28-32)
 2. Docetaxel 20 mg/10 mi/kg, i.p., (q7dx3, days 14, 21, 28).
 3. Combination groups: 7-t-butoxyiminomethylcamptothecin+docetaxel 0.17+20.

Data Analysis

All raw data are recorded on appropriate forms bound in numbered registers, stored and processed by a computer system. The formula TV (mm3)=length (mm)×width (mm)2]/2 is used, where the width and the length are the shortest and the longest diameters of each tumor, respectively. LCK (log10 cell kill) is calculated using the following formula: (T−C)/3.32×DT where T−C are the mean time (in days) required for treated (T) and control (C) tumors, respectively, to reach a determined volume, and DT is the doubling time of control tumors. CR is defined as disappearance of the tumor lasting at least 10 days after the end of treatments. The effect of the combination of 7-t-butoxyiminomethylcamptothecin and the different agents is evaluated according to the method of Romanelli et al. (1998) Cancer Chemother. Pharmacol. 41, 385-390. An R index of 1 (additive effect) or lower indicates the absence of synergism. Synergism is defined as any value of R greater than unity. R was calculated from expected and observed T/C % values.

MCF-7 estrogen-dependent breast carcinoma: 7-t-butoxyiminomethylcamptothecin delivered p.o. according to the schedule qdx5 at 0.28 mg/kg (MTD) shows a potent antitumor activity (TVI=70%) with 1 out of 8 mice without tumor lesion 32 days after the last treatment. On the same tumor model, docetaxel at the MTD of 20 mg/kg, i.p. q4dx2, shows a comparable antitumor activity to that of 7-t-butoxyiminomethylcamptothecin (TVI=73%) and CR=1/8. When 7-t-butoxyiminomethylcamptothecin is combined with docetaxel, both at their MTD, a strong toxicity is observed (7/8 mice died), whereas at their suboptimal doses (0.19+13.3 mg/kg) a synergistic interaction (R=9.5) was found in terms of increase in tumor volume inhibition and in number of complete responses.

Antitumor activity of 7-t-butoxyiminomethylcamptothecin [A]
(p.o., qdx5/w, +6) in combination with docetaxel [B]
(i.p., q3-4dx2, +6) against MCF-7 human breast ca.

| Drug  | Dose (mg/kg) | BWL %[1] | Tox[2] | TVI %[3] | CR  |
|-------|--------------|----------|--------|----------|-----|
| A     | 0.28         | 9        | 1/8    | 70       | 1/8 |
| A     | 0.19         | 10       | 2/8    | 81       | 1/8 |
| B     | 13.3         | 4        | 1/8    | 0        | 1/8 |
| B     | 20           | 7        | 0/8    | 73       | 1/8 |
| B + A | 13.3 + 0.19  | 12       | 3/8    | 98       | 5/8 |
| B + A | 20 + 0.19    | 15       | 3/8    | 96       | 2/8 |
| B + A | 13.3 + 0.28  | 14       | 2/8    | 96       | 2/8 |
| B + A | 20 + 0.28    | 31       | 7/8    | /        | 1/8 |

Treatment starts 6 days after the tumor injection.
[1]Body weight loss % induced by drug treatment.
[2]Dead/treated mice.
[3]Tumor volume inhibition % in treated over control tumors.
[4]LCK = log10 cell kill.
[5]CR = complete response. DT = 18.9 days. R = 7.5 (0.28 + 13.3); R = 9.5 (0.19 + 13.3); R = 1.3 (0.19 + 20).

A2780/DDP platinum-resistant ovarian carcinoma: 7-t-butoxyiminomethylcamptothecin at the approximate maximum tolerated dose of 0.28 mg/kg (qdx5/w) is slightly efficacious (TVI=46%). Docetaxel (20 mg/kg, i.p., q4dx2) at the MTD shows a comparable antitumor effect to that of 7-t-butoxyiminomethylcamptothecin. The effect of the combination of 7-t-butoxyiminomethylcamptothecin with docetaxel is additive on this tumor model.

Antitumor activity of 7-t-butoxyiminomethylcamptothecin [A] (p.o.,
qdx5/w, +3) in combination with docetaxel [B] (i.p., q4dx2, +3)
against A2780/DDP platinum-resistant ovarian carcinoma

| Drug  | Dose (mg/kg) | BWL %[1] | Tox[2] | TVI %[3] | LCK[4] |
|-------|--------------|----------|--------|----------|--------|
| A     | 0.19         | 1        | 0/8    | 35       | 0.18   |
| A     | 0.28         | 7        | 0/8    | 46       | 0.23   |
| B     | 13.3         | 8        | 0/8    | 7        | 0.09   |
| B     | 20           | 17       | 0/8    | 43       | 0.18   |
| B + A | 13.3 + 0.19  | 12       | 0/8    | 43       | 0.62   |
| B + A | 20 + 0.19    | 14       | 0/8    | 23       | 0.18   |
| B + A | 13.3 + 0.28  | 13       | 0/8    | 54       | 0.62   |
| B + A | 20 + 0.28    | 19       | 0/8    | 65       | 0.71   |

Treatment starts 3 days after the tumor injection.
[1]Body weight loss % induced by drug treatment.
[2]Dead/treated mice.
[3]Tumor volume inhibition % in treated over control tumors.
[4]LCK = log10 cell kill. DT = 1.7 days. R = 1.06 (13.3 + 0.19); 0.48 (20 + 0.19); 1.09 (13.3 + 0.28); 0.88 (20 + 0.28).

NCI-H460 NSCLC: 7-t-butoxyiminomethylcamptothecin (0.28 mg/kg, p.o., qdx5) reveals a stronger antitumor effect (TVI=94%) compared with docetaxel (20 mg/kg, i.p. q4dx2) (TVI=63% and 1 out of 8 mice with complete response 10 days after the last treatment). The interaction of 7-t-butoxyiminomethylcamptothecin with docetaxel is additive or synergistic depending on the dose regiment.

Antitumor activity of 7-t-butoxyiminomethylcamptothecin [A] (p.o.,
qdx5/w, +3) in combination with docetaxel [B] (i.p., q4dx2, +3)
against NCI-H460 non-small cell lung carcinoma

| Drug  | Dose (mg/kg) | BWL %[1] | Tox[2] | TVI %[3] | CR[4] | LCK[5] |
|-------|--------------|----------|--------|----------|-------|--------|
| A     | 0.19         | 8        | 0/8    | 79       | 1/8   | 1.14   |
| A     | 0.28         | 16       | 1/8    | 94       | 0/8   | 1.45   |
| B     | 13.3         | 2        | 0/8    | 4        | 0/8   | 0.21   |
| B     | 20           | 7        | 0/8    | 63       | 1/8   | 0.72   |
| B + A | 13.3 + 0.19  | 8        | 0/8    | 87       | 0/8   | 1.87   |
| B + A | 20 + 0.19    | 9        | 0/8    | 94       | 0/8   | 1.87   |
| B + A | 13.3 + 0.28  | 16       | 0/8    | 95       | 1/8   | 2.3    |
| B + A | 20 + 0.28    | 18       | 0/8    | 95       | 0/8   | 1.87   |

Treatment starts 3 days after the tumor injection.
[1]Body weight loss % induced by drug treatment.
[2]Dead/treated mice.
[3]Tumor volume inhibition % in treated over control tumors.
[4]CR = complete response after the last treatment.
[5]LCK = log10 cell kill. DT = 2.9 days. R = 1.5 (13.3 + 0.19); 1.3 (20 + 0.19); 1.15 (13.3 + 0.28); 0.44 (20 + 0.28).

DU145 prostate carcinoma: 7-t-butoxyiminomethylcamptothecin at the approximate maximum tolerated dose of 0.25 mg/kg (qdx5/w) shows an activity comparable to that found with the MTD of docetaxel delivered i.p. at 20 mg/kg, q4dx2 (TVI was 53%). The combination of the suboptimal doses of docetaxel with 7-t-butoxyiminomethylcamptothecin (13.3 and 0.19 mg/kg) produces a synergistic interaction. When 7-t-butoxyiminomethylcamptothecin is given for 3 weeks at the suboptimal dose of 0.17 mg/kg in combination with docetaxel at 20 mg/kg, i.p. (q7dx3), it produces a synergistic effect on tumor growth in terms of complete responses (3/8) and increase in LCK.

Antitumor activity of 7-t-butoxyiminomethylcamptothecin [A] (p.o.,
qdx5/w, +14) in combination with docetaxel [B] (i.p., q4dx2, +14)
against DU145 prostate carcinoma

| Drug  | Dose (mg/kg) | BWL %[1] | Tox[2] | TVI %[3] | CR[4] | LCK[5] |
|-------|--------------|----------|--------|----------|-------|--------|
| A     | 0.19         | 4        | 0/8    | 25       | 0/8   | 0.28   |
| A     | 0.25         | 8        | 0/8    | 53       | 0/8   | 0.28   |
| B     | 13.3         | 0        | 0/8    | 23       | 0/8   | 0.28   |
| B     | 20           | 8        | 0/8    | 68       | 0/8   | 0.65   |
| B + A | 13.3 + 0.19  | 9        | 0/8    | 70       | 0/8   | 0.65   |
| B + A | 13.3 + 0.25  | 11       | 0/8    | 66       | 0/8   | 0.65   |

Treatment starts 14 days after the tumor injection.
[1]Body weight loss % induced by drug treatment.
[2]Dead/treated mice.
[3]Tumor volume inhibition % in treated over control tumors.
[4]CR = complete response after the last treatment.
[5]LCK = log10 cell kill. DT = 10.7 days. R = 1.92 (13.3 + 0.19); 1.06 (13.3 + 0.25).

EXAMPLE 3

Combination of 7-t-butoxyiminomethylcamptothecin and Paclitaxel

In Vivo Experimental Procedures

Test system: Female CD1 nu/nu mice for tumor models were used.

Number of animals: 176 (88 for each tumor model)

NCI-H460 human lung carcinoma from in vitro cell cultures are injected s.c. using 3×106 cells/100 µl/mouse into the right flank of CD1 nude mice. Mice are treated with 3 intravenously doses of paclitaxel at days 3, 10, 17 after tumor injection. 7-t-butoxyiminomethylcamptothecin is administered by oral route for 3 cycles (qdx5/w) starting 3 days after the tumor implantation. In other groups of mice 7-t-butoxyiminomethylcamptothecin is given p.o. in combination with paclitaxel by using the same schedule. Treatments in NCI-H460 tumor model are performed in the following groups of 8 mice each:

1. Vehicle
2. 50 mg/15 ml/kg, i.v. of paclitaxel (3, 10, 17)
3. 33.3 mg/15 ml/kg, i.v. of paclitaxel (3, 10, 17)
4. 25 mg/15 ml/kg, i.v. of paclitaxel (3, 10, 17)
5. 7-t-butoxyiminomethylcamptothecin 0.25 mg/10 ml/kg, p.o. (3-7), (10-14), (17-21)
6. 7-t-butoxyiminomethylcamptothecin 0.125 mg/10 ml/kg, p.o. (3-7), (10-14), (17-21)
7. 7-t-butoxyiminomethylcamptothecin 0.08 mg/10 ml/kg, p.o. (3-7), (10-14), (17-21)
8. Paclitaxel+7-t-butoxyiminomethylcamptothecin (33.3+0.125)
9. Paclitaxel+7-t-butoxyiminomethylcamptothecin (33.3+0.08)
10. Paclitaxel+7-t-butoxyiminomethylcamptothecin (25+0.125)
11. Paclitaxel+7-t-butoxyiminomethylcamptothecin (25+0.08)

To evaluate the antitumor activity of drugs on human xenografts, tumor volume is evaluated by measuring biweekly tumor diameters with a Vernier caliper. The formula TV (mm3)=[length (mm)×width (mm)2]/2 is used, where the width and the length are the shortest and the longest diameters of each tumor, respectively. When tumors of mice achieved a volume of about 2 g, the animals are sacrificed by cervical dislocation.

Data Analysis

All raw data are recorded on appropriate forms bound in numbered registers, stored and processed by a computer system. The formula TV (mm3)=length (mm)×width (mm)2]/2 is used, where the width and the length are the shortest and the longest diameters of each tumor, respectively. LCK (10 cell kill) is calculated using the following formula: (T−C)/3.32×DT where T−C are the mean time (in days) required for treated (T) and control (C) tumors, respectively, to reach a determined volume, and DT is the doubling time of control tumors. CR is defined as disappearance of the tumor lasting at least 10 days after the end of treatments. The effect of the combination of 7-t-butoxyiminomethylcamptothecin and the different agents is evaluated according to the method of Romanelli et al. (1998). An R index of 1 (additive effect) or lower indicates the absence of synergism. Synergism is defined as any value of R greater than unity. R is calculated from expected and observed T/C % values.

NCI-H460 tumor model: at the tolerated dose of paclitaxel of 50 mg/kg, i.v. administered according to the schedule q7dx3, starting 3 days after tumor inoculum, is able to induce a reduction of tumor growth (T/C %=38.6), with a low mean weight loss of 6%. The other two low doses of 33.3 mg/kg and 25 mg/kg, which are ⅔ of MTD and ½ of MTD, respectively, given i.v. according to the same schedule, are effective too. The T/C % evaluated are 36.8 and 55.2, respectively. The NCI-H460 tumor is very responsive to 7-t-butoxyiminomethylcamptothecin alone, since both the doses of 0.25 mg/kg and 0.125 mg/kg, administered for 5 days for 3 cycles, reduce the tumor volume of about 99% and 90%, respectively (T/C % were 1.5 and 9.9). These doses did not produce toxicity-related deaths (0 out of 8 mice) or reduction of body weight. A minor dose of 7-t-butoxyiminomethylcamptothecin (0.08 mg/kg), given according to the same schedule, is effective (T/C %=59.5%). When suboptimal doses of each drug are combined (0.125 mg/kg of 7-t butoxyiminomethylcamptothecin and 33.3 or 25 mg/kg of paclitaxel), the combination groups achieve a tumor growth inhibition higher than with that achieved by the single-agent 7-t-butoxyiminomethylcamptothecin therapy (T/C % were 2.2 and 2.5%), with R index values of 1.6 and 2.2, respectively. These treatments did not induce toxicity in mice. Also the combination of a lower dose of 7-t-butoxyiminomethylcamptothecin (0.08 mg/kg) with the two suboptimal doses of paclitaxel (33.3 and 25 mg/kg, i.v.) produce R index values of 1.3 and 2.1.

Antitumor activity of 7-t-butoxyiminomethylcamptothecin [A] (p.o., qdx5/w, +3) in combination with paclitaxel [B] (i.v., q7dx3, +3) against NCI-H460 NSCLC

| Drug | Dose (mg/kg) | BWL %[1] | Tox[2] | T/C %[3] | R |
|---|---|---|---|---|---|
| A | 0.25 | 0 | 0/8 | 1.5 | |
| A | 0.125 | 0 | 0/8 | 9.9 | |
| A | 0.08 | 0 | 0/8 | 59.5 | |
| B | 50 | 6 | 0/7 | 38.6 | |
| B | 33.3 | 2 | 0/8 | 36.8 | |
| B | 25 | 1 | 0/8 | 55.2 | |
| B + A | 33.3 + 0.125 | 3 | 1/8 | 2.2 | 1.6 |
| B + A | 25 + 0.125 | 6 | 0/7 | 2.5 | 2.2 |
| B + A | 33.3 + 0.08 | 2 | 0/8 | 20.9 | 1.3 |
| B + A | 25 + 0.08 | 3 | 0/7 | 15.7 | 2.1 |

[1]Body weight loss % induced by drug treatment.
[2]Dead/treated mice.
[3]TW in treated mice/TW in control mice × 100.

EXAMPLE 4

Combination of 7-t-butoxyiminomethylcamptothecin and Carboplatin

In Vivo Experimental Procedures

Test system: Female CD1 nu/nu mice for tumor models are used.

Number of animals: 176 (88 for each tumor model)

A2780/DDP human platinum ovarian carcinoma cells (2×106) are implanted in the right flank of female mice. 8 mice/group are treated 3 days after tumor injection with the following drugs.

1. Vehicle
2. 7-t-butoxyiminomethylcamptothecin 0.28 mg/10 ml/kg and 0.19 mg/10 mi/kg p.o. (qdx5/w, days 3-7)
3. Carboplatin 50 mg/10 ml/kg and 33.3 mg/10 ml/kg, i.p. (q4dx2, days 3, 7)
4. Combination groups 7-t-butoxyiminomethylcamptothecin+carboplatin: 0.28+50, 0.28+33.3, 0.19+50, 0.19+33.3.

A2780 ovarian carcinoma cells (2×106) are implanted s.c. in the right flank of female mice. 7-8 mice/group are treated 3 days after tumor injection with the following drugs.

1. Vehicle
2. 7-t-butoxyiminomethylcamptothecin 0.28 mg/10 ml/kg and 0.19 mg/10 ml/kg, p.o. (qdx5/w, days 3-7)
3. Carboplatin 50 mg/10 ml/kg and 33.3 mg/10 ml/kg, i.p. (q4dx2, days 3, 7)
4. Combination groups: 7-t-butoxyiminomethylcamptothecin+carboplatin: 0.28+50, 0.28+33.3, 0.19+50, 0.19+33.3.
5. 7-T-butoxyiminomethylcamptothecin 0.19 mg/10 ml/kg, p.o. (qdx5/wx2w, days 3-7, 10-14).
6. Carboplatin 50 mg/10 ml/kg, i.p. (q7dx2, days 3, 10).
7. Combination groups: 7-t-butoxyiminomethylcamptothecin+carboplatin 0.19+50.

NCI-H460 human non-small cell lung carcinoma cells (3×106) are implanted in the right flank of female mice. 8 mice/group are treated 3 days after tumor injection with the following drugs:

1. Vehicle
2. 7-t-butoxyiminomethylcamptothecin 0.28 mg/10 ml/kg and 0.19 mg/10 ml/kg p.o. (qdx5/w, days 3-7)
3. Carboplatin 50 mg/10 ml/kg and 33.3 mg/10 ml/kg, i.p. (q4dx2, days 3, 7)
4. Combination groups: 7-t-butoxyiminomethylcamptothecin+carboplatin: 0.28+50, 0.28+33.3, 0.19+50, 0.19+33.3.

7 mice/group are also treated 3 days after tumor injection with the following drugs:

1. 7-t-butoxyiminomethylcamptothecin 0.19 mg/10 ml/kg, p.o. (qdx5/wx2w, days 3-7, 10-14)
2. Carboplatin 50 mg/10 ml/kg, i.p. (q7dx2, days 3, 10)

In all the combination groups, the drug were administered 1 h before 7-t butoxyiminomethylcamptothecin.

To evaluate the antitumor activity of drugs on human xenografts, tumor volume is evaluated by measuring biweekly tumor diameters with a Vernier caliper. The formula TV (mm3)=[length (mm)×width (mm)2]/2 is used, where the width and the length are the shortest and the longest diameters of each tumor, respectively. When tumors of mice achieve a volume of about 2 g, the animals are sacrificed by cervical dislocation.

Data Analysis

All raw data are recorded on appropriate forms bound in numbered registers, stored and processed by a computer system. The formula TV (mm3)=length (mm)×width (mm)2]/2 is used, where the width and the length are the shortest and the longest diameters of each tumor, respectively. LCK (log10 cell kill) is calculated using the following formula: (T−C)/3.32×DT where T−C are the mean time (in days) required for treated (T) and control (C) tumors, respectively, to reach a determined volume, and DT is the doubling time of control tumors. CR is defined as disappearance of the tumor lasting at least 10 days after the end of treatments. The effect of the combination of 7-t-butoxyiminomethylcamptothecin and the different agents is evaluated according to the method of Romanelli et al. (1998). An R index of 1 (additive effect) or lower indicates the absence of synergism. Synergism is defined as any value of R greater than unity. R is calculated from expected and observed T/C % values.

A2780/DDP platinum-resistant ovarian carcinoma tumor model: 7-t-butoxyiminomethylcamptothecin at the approximate maximum tolerated dose of 0.28 mg/kg (qdx5/w) is slightly efficacious (TVI=46%) and showed a comparable activity to that of carboplatin (50 mg/kg, i.p., q4dx2) (TVI=34%). When 7-t-butoxyiminomethylcamptothecin is combined with carboplatin, an additive to synergistic interaction is found.

Antitumor activity of 7-t-butoxyiminomethylcamptothecin [A] (p.o., qdx5/w, +3) in combination with carboplatin [B] (i.p., q4dx2, +3) against A2780/DDP platinum-resistant ovarian carcinoma

| Drug | Dose (mg/kg) | BWL %[1] | Tox[2] | TVI %[3] | LCK[4] |
|---|---|---|---|---|---|
| A | 0.19 | 1 | 0/8 | 35 | 0.18 |
| A | 0.28 | 7 | 0/8 | 46 | 0.23 |
| B | 33 | 4 | 0/8 | 0 | 0 |
| B | 50 | 6 | 0/8 | 34 | 0.26 |
| B + A | 33 + 0.19 | 8 | 0/8 | 28 | 0.39 |
| B + A | 50 + 0.19 | 18 | 0/8 | 40 | 0.39 |
| B + A | 33 + 0.28 | 10 | 0/8 | 60 | 0.57 |
| B + A | 50 + 0.28 | 21 | 0/8 | 62 | 0.80 |

Treatment starts 3 days after the tumor injection.
[1]Body weight loss % induced by drug treatment.
[2]Dead/treated mice.
[3]Tumor volume inhibition % in treated over control tumors.
[4]LCK = log10 cell kill. DT = 1.7 days. R = 0.9 (33 + 0.19); 0.71 (50 + 0.19); 1.35 (33 + 0.28); 0.94 (50 + 0.28).

A2780 ovarian carcinoma tumor model: 7-t-butoxyiminomethylcamptothecin at the MTD of 0.28 mg/kg shows a potent antitumor activity in terms of tumor volume inhibition (TVI=100%), CR=8/8 and LCK>2. When it is combined with carboplatin at the suboptimal dose of 33.3 mg/kg, i.p., q4dx2, an increase of LCK is observed, suggesting a major persistence of the effect in the inhibition of tumor growth after the end of the treatment. A similar result is obtained when 7-t-butoxyiminomethylcamptothecin given for 2 weeks (0.19 mg/kg, qdx5/wx2w) is combined with carboplatin (50 mg/kg, q7dx2), since a higher LCK was reached.

Antitumor activity of 7-t-butoxyiminomethylcamptothecin [A] (p.o., qdx5/w, +3) in combination with carboplatin [B] (i.p., q4dx2, +3) against A2780 ovarian carcinoma

| Drug | Dose (mg/kg) | BWL %[1] | Tox[2] | TVI %[3] | CR[4] | LCK[5] |
|---|---|---|---|---|---|---|
| A | 0.19 | 6 | 0/8 | 100 | 8/8 | 2.15 |
| A | 0.28 | 13 | 0/8 | 100 | 8/8 | 2.44 |
| B | 33.3 | 4 | 0/8 | 82 | 2/8 | 1.0 |
| B | 50 | 5 | 0/8 | 84 | 1/8 | 1.0 |
| B + A | 33.3 + 0.19 | 13 | 0/8 | 100 | 8/8 | 2.87 |
| B + A | 33.3 + 0.28 | 25 | 0/8 | 100 | 8/8 | 4.30 |
| B + A | 50 + 0.19 | 19 | 0/8 | 100 | 8/8 | 3.58 |
| B + A | 50 + 0.28 | 27 | 2/8 | 100 | 6/6 | 5.90 |

Treatment starts 3 days after the tumor injection.
[1]Body weight loss % induced by drug treatment.
[2]Dead/treated mice.
[3]Tumor volume inhibition % in treated over control tumors.
[4]CR = complete response after the last treatment.
[5]LCK = log10 cell kill. DT = 2.1 days. On day +60 the following mice were without tumor lesions: 33.3 + 0.19 (1/8), 50 + 0.19 (2/8), 33.3 + 0.28 (5/8), 50 + 0.28 (3/6).

Antitumor activity of 7-t-butoxyiminomethylcamptothecin [A] (p.o., qdx5/wx2w, +3) in combination with carboplatin [B] (i.p., q7dx2, +3) against A2780 ovarian carcinoma

| Drug | Dose (mg/kg) | BWL %[1] | Tox[2] | TVI %[3] | CR[4] | LCK[5] |
|---|---|---|---|---|---|---|
| A | 0.19 | 6 | 0/7 | 100 | 4/7 | 3.15 |
| B | 50 | 5 | 0/7 | 71 | 1/7 | 1.15 |
| B + A | 50 + 0.19 | 18 | 0/7 | 100 | 7/7 | 5.30 |

Treatment starts 3 days after the tumor injection.
[1]Body weight loss % induced by drug treatment.
[2]Dead/treated mice.
[3]Tumor volume inhibition % in treated over control tumors.
[4]CR = complete response after the last treatment.
[5]LCK = log10 cell kill. DT = 2.1 days. On day +60 the following mice are without tumor lesions: 0.19 (4/7), 50 (1/7), 50 + 0.19 (7/7).

NCI-H460 NSCLC tumor model, 7-t-butoxyiminomethylcamptothecin (0.28 mg/kg, p.o., qdx5) reveals a strong antitumor effect (TVI=94%) compared to carboplatin at 50 mg/kg, i.p. q4dx2, (MTD), with a moderate antitumor effect (TVI=59%). When 7-t-butoxyiminomethylcamptothecin (0.28 mg/kg) is combined with a suboptimal dose of carboplatin (33.3 mg/kg), a synergistic effect (R=3) is observed since TVI reached 100% and 3 out of 8 mice are without tumor lesion 10 days after tumor implantation. A therapeutic advantage is found with this type of combination since it exceeds the efficacy of the two drugs given alone. An additive effect is found with the combination of other doses. 7-t-butoxyiminomethylcamptothecin is also given according to the schedule qdx5/wx2w at 0.19 mg/kg in combination with carboplatin at 50 mg/kg, i.p., q7dx2 still producing a synergistic effect (R=1.9)

Antitumor activity of 7-t-butoxyiminomethylcamptothecin [A] (p.o., qdx5/w, +3) in combination with carboplatin [B] (i.p., q4dx2, +3) against NCI-H460 non-small cell lung carcinoma

| Drug | Dose (mg/kg) | BWL %[1] | Tox[2] | TVI %[3] | CR[4] | LCK[5] |
|---|---|---|---|---|---|---|
| A | 0.19 | 8 | 0/8 | 79 | 1/8 | 1.14 |
| A | 0.28 | 16 | 1/8 | 94 | 0/8 | 1.45 |
| B | 33.3 | 4 | 0/8 | 49 | 0/8 | 0.73 |
| B | 50 | 8 | 0/8 | 59 | 0/8 | 0.83 |
| B + A | 33.3 + 0.19 | 12 | 0/8 | 91 | 0/8 | 1.87 |
| B + A | 50 + 0.19 | 21 | 0/8 | 95 | 0/8 | 1.87 |
| B + A | 33.3 + 0.28 | 26 | 0/8 | 100 | 3/8 | 2.6 |
| B + A | 50 + 0.28 | 25 | 0/8 | 97 | 1/8 | 2.1 |

Treatment starts 3 days after the tumor injection.
[1]Body weight loss % induced by drug treatment.
[2]Dead/treated mice.
[3]Tumor volume inhibition % in treated over control tumors.
[4]CR = complete response after the last treatment.
[5]LCK = log10 cell kill. DT = 2.9 days. R = 1.2 (33.3 + 0.19); 1.7 (50 + 0.19); 3 (33.3 + 0.28); 0.82 (50 + 0.28).

Antitumor activity of 7-t-butoxyiminomethylcamptothecin [A] (p.o., qdx5/wx2w, +3) in combination with carboplatin [B] (i.p., q7dx2, +3) against NCI-H460 non-small cell lung carcinoma

| Drug | Dose (mg/kg) | BWL %[1] | Tox[2] | TVI %[3] | CR[4] | LCK[5] |
|---|---|---|---|---|---|---|
| A | 0.19 | 7 | 0/7 | 94 | 0/7 | 2.3 |
| B | 50 | 3 | 0/7 | 38 | 0/7 | 0.73 |
| B + A | 50 + 0.19 | 18 | 0/7 | 98 | 0/7 | 2.9 |

Treatment starts 3 days after the tumor injection.
[1]Body weight loss % induced by drug treatment.
[2]Dead/treated mice.
[3]Tumor volume inhibition % in treated over control tumors.
[4]CR = complete response after the last treatment. 5LCK = log10 cell kill. DT = 2.9 days. R = 1.86 (50 + 0.19)

EXAMPLE 5

Combination of 7-t-butoxyiminomethylcamptothecin and Doxorubicin

In Vivo Experimental Procedures

Test system: BALB/c nu/nu mice for tumor models are used.

MDA MB 435S human breast cancer cells (passage 4 from working stock VPStock 044) are obtained from ATCC (Rockville, Md., USA) and cultured in RPMI1640 cell culture medium, which is supplemented with 10% FCS and penicillinstreptomycin (50 IU/mL, 50 µg/mL final concentration). The cells are harvested by trypsinisation, washed twice in HBSS and counted using Trypan Blue to distinguish viable cells. The cells are then resuspended in HBSS and adjusted to a final concentration of 1×107 cells/mL. For inoculation the injection site is liberally swabbed with alcohol and the needle introduced through the skin into the subcutaneous space just below the animal's right shoulder, where 100 µL of cells (1×106) are discharged. Acceptable tumor volumes are reached 30 days post inoculation.

7-t-butoxyiminomethylcamptothecin is administered orally (p.o.) 5 times per week, both on its own (i.e. as a mono-therapy) and in combination with doxorubicin. Doxorubicin (either on its own or in conjunction with Gimatecan) is administered 3 times per week intravenously, via the tail vein (i.v.).

1. Vehicle
2. 7-t-butoxyiminomethylcamptothecin 0.29 mg/kg, 0.17 mg/kg and, 0.09 mg/kg p.o. (qdx5/w)
3. Doxorubicin 50 mg/10 ml/kg and 4.5 mg/kg, 2.97 mg/kg, 1.49 mg/kg, i.v. ((qdx3/w))
4. Combination groups: 7-t-butoxyiminomethylcamptothecin+Doxorubicin: 0.17+2.97, 0.17+1.49, 0.17+0.45, 0.09+2.97, 0.09+1.49, 0.09+2.97, 0.03+2.97, 0.03+1.49, 0.03+0.45

Data Analysis

The paired t-test is used to determine differences in body weight changes from Day 0 to Day 13 for groups 14 and 15 and from Day 0 to Day 20 for all other groups (Table 4). All calculations are done using SigmaStat 3.0. The one way ANOVA procedure is used for statistical calculations of differences in the tumor volumes.

MDA MB 435S human breast cancer, 7-t-butoxyiminomethylcamptothecin in combination with doxorubicin shows additive to synergistic antitumor activity. Synergistic activity is most notable in the B 0.29+A 0.07 group where the single agent non efficacious doses provide a combination activity of 48% T/C.

Antitumor activity of 7-t-butoxyiminomethylcamptothecin [A] (p.o., qdx5/w, +3) in combination with doxorubicin [B] (i.v., qdx3/w, +3) against MDA MB 435S human breast cancer

| Drug | Dose (mg/kg) | BWL %[1] | Tox[2] | T/C %[3] |
|---|---|---|---|---|
| A | 0.21 | 1 | 1/9 | 5 |
| A | 0.14 | 1 | 0/9 | 46 |
| A | 0.07 | (+2.5) | 9/9 | 93 |
| B | 2.9 | 9.9 | 9/9 | 45 |
| B | 1.91 | 8.4 | 8/9 | 51 |
| B | 0.96 | (+2.5) | 9/9 | 78 |
| B + A | 1.91 + 0.14 | 16 | 9/9 | 5 |
| B + A | 0.96 + 0.14 | 4.4 | 9/9 | 30 |
| B + A | 0.29 + 0.14 | 3.5 | 9/9 | 43 |
| B + A | 1.91 + 0.07 | 6 | 9/9 | 42 |
| B + A | 0.96 + 0.07 | 3.5 | 9/9 | 41 |
| B + A | 0.29 + 0.07 | (+3.4) | 9/9 | 48 |
| B + A | 1.91 + 0.03 | 2.6 | 8/9 | 68 |

[1]Body weight loss % induced by drug treatment.
[2]Dead/treated mice.
[3]Tumor volume inhibition % treated over control tumors.

EXAMPLE 6

Combination of 7-t-butoxyiminomethylcamptothecin and cis-Platinum

In Vitro Experimental Procedures
Cell Culture and Cytotoxicity Assay

NCI-H460 non-small cell lung carcinoma (NSCLC) is obtained from the American Type Culture Collection (ATCC), A549 (NSCLC), HT-29 colon adenocarcinoma, A2780 and A2780/Dx, A2780/DDP ovarian carinomas are from Istituto Nazionale Tumori, Milan, Italy. Cells are grown in RPMI 1640 (GIBCO) containing 10% fetal bovine serum (GIBCO) and 50 µg/ml gentamycin sulfate (SIGMA). In order to test the effects of chemotherapeutic agents on cell growth, cells are seeded in 96-well tissue culture plates (Corning) at approximately 10% confluence and are allowed to attach and recover for at least 24 h. Varying concentrations of drugs alone or combined each other are then added to each well. The plates are incubated for 2 h and then washed before being incubated without drugs for additional 72 h. Other plates are treated with drugs sequentially (2 h with a drug followed by the other drug for 72 h). The number of surviving cells are then determined by staining with sulforhodamine B (SRB) as described by Skehan P et al. (1990) J. Natl. Cancer Inst. 82, 1107-1112.

Data Analysis

The interaction between 7-t-butoxyiminomethylcamptothecin and the different drugs is determined by using the analysis of Drewinko et al. (1976) Cancer Biochem. Biophys. 1: 187-195. The analysis is performed as follows: (SFaxSFb/SFa+SFb)/100, where SFa is the survival fraction of 7-t-butoxyiminomethylcamptothecin and SFb is the survival fraction of the chemotherapeuticagent. Values indicated the following effects: a value>1 synergism, <1 antagonism, =1 additive.

NCI-H460 non-small cell lung carcinoma: when cells are exposed simultaneously or sequential, the combination shows an additive cytotoxic effect (R index of 1).

A549 non-small cell lung carcinoma: when cells are simultaneously exposed to 7-t-butoxyiminomethylcamptothecin and cis-Platinum, or to a sequential treatment of cis-Platinum followed by 7-t-butoxyiminomethylcamptothecin show an additive cytotoxic effect, (R index of 1). When A549 cells are sequentially exposed to 7-t-butoxyiminomethylcamptothecin followed by cis-Platinum, a synergistic cytotoxic effect (R values of 1.2-1.3) is observed.

A2780 ovarian carcinoma: when cells were exposed simultaneously or sequential, the combination shows an additive cytotoxic effect (R index of 1).

A2780/DDP (Platinum resistant) ovarian carcinoma: when cells are exposed simultaneously or in the sequence cis-Platinum followed by 7-t-butoxyiminomethylcamptothecin, the combination shows an additive cytotoxic effect (R index of 1). When a2780/DDP cells are sequentially exposed to 7-t-butoxyiminomethylcamptothecin followed by cis-Platinum, a synergistic cytotoxic effect (R values of 1.2) is observed.

| Cell line | R value mean | Schedule | Comments |
|---|---|---|---|
| H460 NSCLC | 1 | ABC | |
| A549 NSCLC | 1 | AC | |
| A549 NSCLC | 1.2-1.3 | B | |
| A2780 ovarian | 1 | ABC | |
| A2780DDP ovarian | 1 | AC | Pt resistant cell line |
| A2780DDP ovarian | 1.2 | B | Pt resistant cell line |

Schedules: (A) 7-t-butoxyiminomethylcamptothecin + cis-Platinum
(B) 7-t-butoxyiminomethylcamptothecin first then cis-Platinum
(C) cis-Platinum first then 7-t-butoxyiminomethylcamptothecin

EXAMPLE 7

Combination of 7-t-butoxyiminomethylcamptothecin and Temozolamide

EXAMPLE 8

Combination of 7-t-butoxyiminomethylcamptothecin and Imatinib

In Vitro Experimental Procedures
Cell Culture and Cytotoxicity Assay

A549 non-small cell lung carcinoma, A375 melanoma, 786-0 renal cell adenocarcinoma SKOV3 ovary adenocarcinoma, 786-O renal cell adenocarcinoma, PANC-1 pancreas epithelioid carcinoma, U266B1 myeloma, SW620 colorectal adenocarcinoma, HeLa Cervical carcinoma and MIA PaCa-2 pancreatic carcinoma is obtained from the American Type Culture Collection (ATCC). The cell line of choice is diluted in appropriate media based on a cell count of 1,000-2,000 cells per well for adherent cell lines and 10,000-20,000 cells per well for suspension cell lines, cells are plated into 96 well plates using 100 ul of the diluted cells per well. 4. The cells are grown overnight in an incubator at 37 deg C., 5% CO2 and 85% humidity prior to drug treatment. Compound dilutions are made from DMSO solutions for each compound. Typically these are centered on the EC50 and could be 6 or 9 dilutions which covered the full dose response of the cell when exposed to the compound. There was a third series of dilutions made for the combination of the two compounds. For every dilution point in this series a fixed ratio of each compound is used. The cells are exposed simultaneously to the compounds for 72 hours and then the amount of proliferation is measured with Alamar Blue fluorescence (ex 535 em 590) for each well using an Envision (PerkinElmer) microplate reader.

Data Analysis

The interaction between 7-t-butoxyiminomethylcamptothecin and the different drugs is determined from the percent inhibition of proliferation defined as the ratio of the endpoint determination in each well divided by the control wells. The combination index (CI) is then determined for the 25, 50 and 75% effect levels as described by Chou and Talay (Chou T-C, Talalay, P. Quantitative analysis of dose-effect relationships: the combined effects of multiple drugs or enzyme inhibitors. Adv. Enzyme Regulation 1984;22:27-55). CI of <1 indicates synergistic cytotoxic effect, CI=1 indicates additive cytotoxic effect and CI>1 indicates an antagonistic cytotoxic effect A549 non-small cell lung carcinoma: combination with Imatinib showed a spectrum of activity from synergistic to antagonistic depending on the concentration of drug used.

SKOV3 ovary adenocarcinoma: combination with Imatinib showed a synergistic cytotoxic effect as indicated by CI values<1

786-O renal cell adenocarcinoma: combination with Imatinib showed a synergistic cytotoxic effect as indicated by CI values<1

MIA PaCa-2 pancreatic carcinoma: combination with Imatinib showed a synergistic or additive cytotoxic effect as indicated by CI values<1 or =1 depending on the concentration of drug used.

A375 melanoma: combination with Imatinib showed a synergistic or additive cytotoxic effect as indicated by CI values<1 or =1 depending on the concentration of drug used.

PANC-1 pancreas epithelioid carcinoma: combination with Imatinib showed an additive cytotoxic effect as indicated by CI values=1

| 7-t-butoxyiminomethylcamptothecin in combination with Imatinib | | | |
|---|---|---|---|
| | Combination Index at cell fraction affected (cell kill) | | |
| Tumor cell line | 25% | 50% | 75% |
| A549 | 0.32 | 0.67 | 1.95 |
| SKOV3 | 0.88 | 0.86 | 0.88 |
| 786-O | 0.78 | 0.92 | 0.62 |
| MIA PaCa-2 | 0.62 | 0.76 | 1.03 |

-continued 7-t-butoxyiminomethylcamptothecin in combination with Imatinib

| Tumor cell line | Combination Index at cell fraction affected (cell kill) | | |
|---|---|---|---|
| | 25% | 50% | 75% |
| A375 | 1.00 | 0.88 | 0.63 |
| PANC-1 | 0.94 | 0.98 | 1.01 |

EXAMPLE 9

Combination of 7-t-butoxyiminomethylcamptothecin and Velcade

In Vitro Experimental Procedures
Cell Culture and Cytotoxicity Assay

A549 non-small cell lung carcinoma, A375 melanoma, 786-0 renal cell adenocarcinoma SKOV3 ovary adenocarcinoma, 786-O renal cell adenocarcinoma, PANC-1 pancreas epithelioid carcinoma, U266B1 myeloma, SW620 colorectal adenocarcinoma, HeLa Cervical carcinoma and MIA PaCa-2 pancreatic carcinoma is obtained from the American Type Culture Collection (ATCC). The cell line of choice is diluted in appropriate media based on a cell count of 1,000-2,000 cells per well for adherent cell lines and 10,000-20,000 cells per well for suspension cell lines, cells are plated into 96 well plates using 100 ul of the diluted cells per well. 4. The cells are grown overnight in an incubator at 37 deg C., 5% CO2 and 85% humidity prior to drug treatment. Compound dilutions are made from DMSO solutions for each compound. Typically these are centered on the EC50 and could be 6 or 9 dilutions which cover the full dose response of the cell when exposed to the compound. There is a third series of dilutions made for the combination of the two compounds. For every dilution point in this series a fixed ratio of each compound is used. The cells are exposed simultaneously to the compounds for 72 hours and then the amount of proliferation is measured with Alamar Blue fluorescence (ex 535 em 590) for each well using an Envision (PerkinElmer) microplate reader.

Data Analysis

The interaction between 7-t-butoxyiminomethylcamptothecin and the different drugs is determined from the percent inhibition of proliferation defined as the ratio of the endpoint determination in each well divided by the control wells. The combination index (CI) is then determined for the 25, 50 and 75% effect levels as described by Chou and Talay (Chou T-C, Talalay, P. Quantitative analysis of dose-effect relationships: the combined effects of multiple drugs or enzyme inhibitors. Adv. Enzyme Regulation 1984;22:27-55). CI of <1 indicates synergistic cytotoxic effect, CI=1 indicates additive cytotoxic effect and CI>1 indicates an antagonistic cytotoxic effect U266B1 myeloma: combination with Velcade shows a spectrum of activity from synergistic to antagonistic depending on the concentration of drug used.

SKOV3 ovary adenocarcinoma: combination with Velcade shows a synergistic cytotoxic effect as indicated by CI values<1.

A375 melanoma: combination with Velcade shows a spectrum of activity from synergistic to antagonistic depending on the concentration of drug used.

MIA PaCa-2 pancreatic carcinoma: combination with Velcade shows an additive cytotoxic effect as indicated by CI values around 1.

SW620 colorectal adenocarcinoma: combination with Velcade shows a spectrum of activity from synergistic to antagonistic depending on the concentration of drug used.

7-t-butoxyiminomethylcamptothecin in combination with Velcade

| Tumor cell line | Combination Index at cell fraction affected (cell kill) | | |
|---|---|---|---|
| | 25% | 50% | 75% |
| U266B1 | 0.41 | 1.19 | 3.48 |
| SKOV3 | 0.87 | 0.61 | 0.55 |
| A375 | 1.23 | 0.85 | 0.66 |
| MIA PaCa-2 | 1.16 | 0.97 | 1.15 |
| SW620 | 1.39 | 0.75 | 0.88 |

EXAMPLE 10

Combination of 7-t-butoxyiminomethylcamptothecin and Epothilone B

In Vitro Experimental Procedures
Cell Culture and Cytotoxicity Assay

Human non-small cell lung adenocarcinoma A549 (CCL 185) and ovarian carcinoma SK-OV-3 (ATCC HTB 77) cell lines are obtained from the American Type Culture Collection (ATCC, Rockville, Md., USA). The human metastatic prostate carcinoma PC-3M is obtained from Dr. I. J. Fidler (MD Anderson Cancer Center, Houston, Tex., USA). Cell culture media and supplements are from Animed/Bioconcept (Allschwil, Switzerland).

Cells are cultured with RPMI-1640 medium (complemented with 10% FCS, penicillin (100 IU/ml), streptomycin (100 µg/ml) and L-glutamine (2 mM)) at 37° C. in an incubator with a 5% v/v $CO_2$ and 80% relative humidity atmosphere. Inhibition of monolayer cell proliferation by test compounds is assessed by methylene blue staining of fixed. Cells are seeded on day 0 at $1.5 \times 10^3$ cells/well into 96-well microtiter plates and incubated overnight. Drug interactions of Epothilone B and the combination partner are assessed under conditions of simultaneous as well as sequential drug addition as follows. Simultaneous drug addition: Epothilone B and the combination partner are concomitantly added on day 1 and antiproliferative effects are assessed after incubation for 72 hrs on day 4. Sequential drug addition, a) "Epothilone B before combination partner": Epothilone B is added on day 1. After incubation for 24 hours, drug-containing medium is removed by aspiration on day 2 and replaced with medium containing the combination partner. Following additional incubation for 48 hrs, antiproliferative effects are assessed on day 4. Sequential drug addition, b) "Epothilone B after combination partner": The combination partner is added on day 1. After incubation for 24 hours, drug-containing medium is removed by aspiration on day 2 and replaced with medium containing Epothilone B. Following additional incubation for 48 hrs, antiproliferative effects are assessed on day 4. Epothilone B and the combination partner are tested at fixed ratios (multiples and fractions) of their respective single agent $IC_{50}$s on a given schedule, as determined in pilot experiments. Drugs are pre-mixed at the highest intended concentrations, followed by nine 1.5-fold serial dilutions in deep-well plates. When assessing single agent activities, which is performed in parallel as internal reference in each experiment, the combination partner is replaced by its respective vehicle. Each condition is present in duplicate. At the end of the incubation period, cells are fixed with 3.3% v/v glutaraldehyde, washed with water and stained with 0.05% w/v methylene blue. After washing, the dye is eluted with 3% HCl and the optical density measured at 665 nm with a SpectraMax 340 spectrophotometer (Molecular Devices, Sunnyvale, Calif.).

Combination Index Analysis of Drug Interaction Effects

To determine the nature of the drug interaction (synergism, additivity or antagonism) with respect to in vitro cell growth inhibition, the combination index method based on the median dose effect principle (Chou T C and Talalay P Advanced Enzyme Regulation 1977;22:27-55) is used. This method takes into account the potency of each drug alone and each drug combination, as well as the shape of the dose-effect curves. Mathematical analysis (Chou T C, Motzer R J, Tong Y and Bosl G J Journal of the National Cancer Institute 1994; 86:1517-1524.) is performed using a commercial software (Calcusyn, Biosoft, UK). The Combination Index (CI) is calculated based on the following multiple drug effect equation: $CI=(D)_1/(D_x)_1+(D)_2/(D_x)_2$. $(D)_1$ and $(D)_2$ are the doses of drug 1 and drug 2 in combination that cause x % cell growth inhibition. $(D_x)_1$ and $(D_x)_2$ are the doses of drug 1 and drug 2 alone, respectively, that cause x % cell growth inhibition. CIs of <1 indicate greater than additive effects (synergism; the smaller the value, the greater the degree of synergy), CIs equal to 1 indicate additivity, and CIs>1 indicate antagonism. CI results are presented as mean±standard error of the mean (n=3 independent experiments).

In A549 (CCL 185) non-small cell lung adenocarcinoma SK-OV-3 ovarian carcinoma and PC-3M metastatic prostate carcinoma the combination of 7-t-butoxyiminomethylcamptothecin and Epothilone B show a sequence dependence effect cytotoxic effect in cell culture. Simultaneous addition results in antagonism where as schedules gives additive to synergistic cytotoxic effect.

Antiproliferative Combination Index of 7-t-butoxyiminomethyl-camptothecin and Epothilone B administered concomitantly or sequentially to A549 (lung), PC-3M (prostate), and SK-OV-3 (ovarian) carcinoma cells in vitro.

| Cell line | Fraction affected (cell kill) | Combination Index (Mean ± SEM; n = 3) | | |
|---|---|---|---|---|
| | | Schedule A | Schedule B | Schedule C |
| A549 | 50% | 1.26 ± 0.12 | 0.89 ± 0.05 | 0.84 ± 0.09 |
| | 75% | 1.58 ± 0.18 | 0.94 ± 0.03 | 0.73 ± 0.04 |
| | 90% | 2.20 ± 0.74 | 1.07 ± 0.04 | 1.02 ± 0.22 |
| PC-3M | 50% | 1.48 ± 0.01 | na[a] | 0.57 ± 0.03 |
| | 75% | 1.80 ± 0.05 | na[a] | 0.86 ± 0.05 |
| | 90% | 2.37 ± 0.20 | na[a] | 1.37 ± 0.21 |
| SK-OV-3 | 50% | 1.48 ± 0.03 | 1.35 ± 0.30 | 0.92 ± 0.08 |
| | 75% | 1.22 ± 0.09 | 0.98 ± 0.05 | 0.70 ± 0.11 |
| | 90% | 1.09 ± 0.18 | 1.10 ± 0.13 | 0.93 ± 0.11 |

Schedules: (A) 7-t-butoxyiminomethylcamptothecin + Epothilone B
(B) 7-t-butoxyiminomethylcamptothecin first then Epothilone B
(C) Epothilone B first then 7-t-butoxyiminomethylcamptothecin
Cell kill (fraction affected; corresponding to $IC_{50}$, $IC_{75}$ and $IC_{90}$). The calculated combination index (CI) values are presented as mean ± standard error of the mean (n = 3 independent experiments). Per definition, CI = 1 indicates additivity. CI < 1.0 indicates synergy (the smaller the value, the stronger the degree of synergy), while CI > 1.0 indicates antagonism (the higher the value, the stronger the degree of antagonism).
[a]not applicable, i.e due to narrow range of cellular effects within drug range tested (less than 50% fraction affected), calculated CI values display erroneously large error range and thus are not shown.

EXAMPLE 11

Combination of 7-t-butoxyiminomethylcamptothecin and Everolimus

In Vitro Experimental Procedures
Cell Culture and Cytotoxicity Assay

A549 non-small cell lung carcinoma, A375 melanoma, 786-O renal cell adenocarcinoma SKOV3 ovary adenocarcinoma, 786-O renal cell adenocarcinoma, PANC-1 pancreas epithelioid carcinoma, U266B1 myeloma, SW620 colorectal adenocarcinoma, HeLa Cervical carcinoma and MIA PaCa-2 pancreatic carcinoma are obtained from the American Type Culture Collection (ATCC). The cell line of choice is diluted in appropriate media based on a cell count of 1,000-2,000 cells per well for adherent cell lines and 10,000-20,000 cells per well for suspension cell lines, cells are plated into 96 well plates using 100 ul of the diluted cells per well. 4. The cells are grown overnight in an incubator at 37 deg C., 5% CO2 and 85% humidity prior to drug treatment. Compound dilutions are made from DMSO solutions for each compound. Typically these are centered on the EC50 and could be 6 or 9 dilutions which covered the full dose response of the cell when exposed to the compound. There was a third series of dilutions made for the combination of the two compounds. For every dilution point in this series a fixed ratio of each compound is used. The cells are exposed simultaneously to the compounds for 72 hours and then the amount of proliferation is measured with Alamar Blue fluorescence (ex 535 em 590) for each well using an Envision (PerkinElmer) microplate reader.

Data Analysis

The interaction between 7-t-butoxyiminomethylcamptothecin and the different drugs is determined from the percent inhibition of proliferation defined as the ratio of the endpoint determination in each well divided by the control wells. The combination index (CI) is then determined for the 25, 50 and 75% effect levels as described by Chou and Talay (Chou T-C, Talalay, P. Quantitative analysis of dose-effect relationships: the combined effects of multiple drugs or enzyme inhibitors. Adv. Enzyme Regulation 1984;22:27-55). CI of <1 indicates synergistic cytotoxic effect, CI=1 indicates additive cytotoxic effect and CI>1 indicates an antagonistic cytotoxic effect A549 non-small cell lung carcinoma: combination with everolimus shows a synergistic cytotoxic effect as indicated by CI values<1.

SKOV3 ovary adenocarcinoma: combination with everolimus shows a spectrum of activity from synergistic to additive depending on the concentration of drug used.

PANC-1 pancreas epithelioid carcinoma: combination with everolimus shows a spectrum of activity from synergistic to additive depending on the concentration of drug used.

SW620 colorectal adenocarcinoma: combination with everolimus shows a spectrum of activity from synergistic to additive depending on the concentration of drug used.

| 7-t-butoxyiminomethylcamptothecin in combination with everolimus | | | |
|---|---|---|---|
| | Combination Index at cell fraction affected (cell kill) | | |
| Tumor cell line | 25% | 50% | 75% |
| A549 | 0.51 | 0.14 | 0.50 |
| SKOV3 | 1.03 | 0.61 | 0.59 |
| PANC-1 | 0.84 | 0.89 | 0.95 |
| SW620 | 0.87 | 0.91 | 0.98 |

EXAMPLE 12

Combination of 7-t-butoxyiminomethylcamptothecin and {6-[4-(4-ethyl-piperazin-1-ylmethyl)-phenyl]-7H-pyrrolo[2,3-d]pyrimidin-4-yl]-((R)-1-phenyl-ethyl)-amine In Vitro Experimental Procedures
Cell Culture and Cytotoxicity Assay A549 non-small cell lung carcinoma, A375 melanoma, 786-O renal cell adenocarcinoma SKOV3 ovary adenocarcinoma, 786-O renal cell adenocarcinoma, PANC-1 pancreas epithelioid carcinoma, U266B1 myeloma, SW620 colorectal adenocarcinoma, HeLa Cervical carcinoma and MIA PaCa-2 pancreatic carcinoma is obtained from the American Type Culture Collection (ATCC). The cell line of choice is diluted in appropriate media based on a cell count of 1,000-2,000 cells per well for adherent cell lines and 10,000-20,000 cells per well for suspension cell lines, cells are plated into 96 well plates using 100 ul of the diluted cells per well. 4. The cells are grown overnight in an incubator at 37 deg C., 5% CO2 and 85% humidity prior to drug treatment. Compound dilutions are made from DMSO solutions for each compound. Typically these are centered on the EC50 and could be 6 or 9 dilutions which covered the full dose response of the cell when exposed to the compound. There is a third series of dilutions made for the combination of the two compounds. For every dilution point in this series a fixed ratio of each compound is used. The cells are exposed simultaneously to the compounds for 72 hours and then the amount of proliferation is measured with Alamar Blue fluorescence (ex 535 em 590) for each well using an Envision (PerkinElmer) microplate reader.

Data Analysis

The interaction between 7-t-butoxyiminomethylcamptothecin and the different drugs is determined from the percent inhibition of proliferation defined as the ratio of the endpoint determination in each well divided by the control wells. The combination index (CI) is then determined for the 25, 50 and 75% effect levels as described by Chou and Talay (Chou T-C, Talalay, P. Quantitative analysis of dose-effect relationships: the combined effects of multiple drugs or enzyme inhibitors. Adv. Enzyme Regulation 1984;22:27-55). CI of <1 indicates synergistic cytotoxic effect, CI=1 indicates additive cytotoxic effect and CI>1 indicates an antagonistic cytotoxic effect.

A549 non-small cell lung carcinoma: combination with {6-[4-(4-ethyl-piperazin-1-ylmethyl)-phenyl]-7H-pyrrolo[2,3-d]pyrimidin-4-yl]-((R)-1-phenyl-ethyl)-amine shows a synergistic cytotoxic effect as indicated by CI values<1.

SKOV3 ovary adenocarcinoma: combination with {6-[4-(4-ethyl-piperazin-1-ylmethyl)-phenyl]-7H-pyrrolo[2,3-d]pyrimidin-4-yl]-((R)-1-phenyl-ethyl)-amine shows a spectrum of activity from synergistic to antagonistic depending on the concentration of drug used.

PANC-1 pancreas epithelioid carcinoma: combination with {6-[4-(4-ethyl-piperazin-1-ylmethyl)-phenyl]-7H-pyrrolo[2,3-d]pyrimidin-4-yl]-((R)-1-phenyl-ethyl)-amine shows a spectrum of activity from synergistic to antagonistic depending on the concentration of drug used.

SW620 colorectal adenocarcinoma: combination with {6-[4-(4-ethyl-piperazin-1-ylmethyl)-phenyl]-7H-pyrrolo[2,3-d]pyrimidin-4-yl]-((R)-1-phenyl-ethyl)-amine shows a spectrum of activity from synergistic to antagonistic depending on the concentration of drug used.

MIA PaCa-2 pancreatic carcinoma: combination with {6-[4-(4-ethyl-piperazin-1-ylmethyl)-phenyl]-7H-pyrrolo[2,3-d]pyrimidin-4-yl]-((R)-1-phenyl-ethyl)-amine shows a synergistic cytotoxic effect as indicated by CI values<1.

A375 melanoma: combination with {6-[4-(4-ethyl-piperazin-1-ylmethyl)-phenyl]-7H-pyrrolo[2,3-d]pyrimidin-4-yl]-((R)-1-phenyl-ethyl)-amine shows a synergistic cytotoxic effect as indicated by CI values<1.

HeLa Cervical carcinoma: combination with {6-[4-(4-ethyl-piperazin-1-ylmethyl)-phenyl]-7H-pyrrolo[2,3-d]pyrimidin-4-yl]-((R)-1-phenyl-ethyl)-amine shows a spectrum of activity from synergistic to additive depending on the concentration of drug used.

| 7-t-butoxyiminomethylcamptothecin in combination with {6-[4-(4-ethyl-piperazin-1-ylmethyl)-phenyl]-7H-pyrrolo[2,3-d]pyrimidin-4-yl]-((R)-1-phenyl-ethyl)-amine | | | |
|---|---|---|---|
| | Combination Index at cell fraction affected (cell kill) | | |
| Tumor cell line | 25% | 50% | 75% |
| A549 | 0.13 | 0.26 | 0.54 |
| SKOV3 | 1.30 | 0.93 | 0.66 |
| PANC-1 | 0.10 | 0.45 | 2.01 |
| SW620 | 1.58 | 0.91 | 0.65 |
| MIA PaCa-2 | 0.93 | 0.84 | 0.76 |
| A375 | 0.44 | 0.56 | 0.63 |
| HeLa | 1.08 | 0.50 | 0.50 |

What is claimed is:

1. A method for treating proliferative disease comprising administering pharmaceutically and synergistically effective amounts of a combination of:

(a) 7-t-butoxyiminomethylcamptothecin; and (b) one or more chemotherapeutic agents selected from
paclitaxel, wherein the proliferative disease is non-small cell lung cancer, and the administration is simultaneous, concurrent, separate or sequential;
docetaxel, wherein the proliferative disease is selected from the group consisting of breast cancer, prostate cancer, non-small cell lung cancer and ovarian cancer, and the administration is simultaneous, concurrent, separate or sequential;
epothilone B, wherein the proliferative disease is selected from the group consisting of lung cancer, prostate cancer and ovarian cancer, and the administration is sequential;
cisplatinum, wherein the proliferative disease is non-small cell lung cancer or ovarian cancer and wherein 7-t-butoxyiminomethylcamptothecin is administered followed by cis-platinum;
carboplatin, wherein the proliferative disease is selected from the group consisting of ovarian cancer and non-small cell lung cancer and the administration is simultaneous, concurrent, separate or sequential;
{6-[4-(4-ethyl-piperazin-1-ylmethyl)-phenyl]-7H-pyrrolo[2,3-d]pyrimidin-4-yl]-((R)-1-phenyl-ethyl)-amine, wherein the proliferative disease is selected from lung cancer, melanoma, renal cell adenocarcinoma, ovary adenocarcinoma, renal cell adenocarcinoma, pancreas epithelioid carcinoma, myeloma, colorectal adenocarcinoma, cervical carcinoma and pancreatic carcinoma, and the administration is simultaneous, concurrent, separate or sequential;
everolimus, wherein the proliferative disease is selected from the group consisting of non-small cell lung cancer, ovary adenocarcinoma, pancreas epithelioid carcinoma and colorectal adenocarcinoma, and the administration is simultaneous, concurrent, separate or sequential;
imatinib, wherein the proliferative disease is selected from the group consisting of non-small cell lung cancer, ovary adenocarcinoma, renal cell adenocarcinoma, pancreatic carcinoma, pancreas epithelioid carcinoma and colorectal adenocarcinoma, and the administration is simultaneous, concurrent, separate or sequential; or
bortezomib, wherein the proliferative disease is selected from the group consisting of ovary adenocarcinoma, melanoma and colorectal adenocarcinoma, and the administration is simultaneous, concurrent, separate or sequential.

2. A method for treating a proliferative disease comprising administering pharmaceutically and synergistically effective amounts of a combination of:
(a) 7-t-butoxyiminomethylcamptothecin; and
(b) paclitaxel, wherein the proliferative disease is non-small cell lung cancer, and the administration is simultaneous, concurrent, separate or sequential.

3. A method for treating a proliferative disease comprising administering pharmaceutically and synergistically effective amounts of a combination of:
(a) 7-t-butoxyiminomethylcamptothecin; and
(b) docetaxel, wherein the proliferative disease is selected from the group consisting of breast cancer, prostate cancer, non-small cell lung cancer and ovarian cancer, and the administration is simultaneous, concurrent, separate or sequential.

4. A method for treating a proliferative disease comprising administering pharmaceutically and synergistically effective amounts of a combination of:
(a) 7-t-butoxyiminomethylcamptothecin; and
(b) epothilone B, wherein the proliferative disease is selected from the group consisting of lung cancer, prostate cancer and ovarian cancer, and the administration is sequential.

5. The method of claim 4 wherein epothilone B is administered first, followed by 7-t-butoxyiminomethylcamptothecin.

6. A method for treating a proliferative disease comprising administering pharmaceutically and synergistically effective amounts of a combination of:
(a) 7-t-butoxyiminomethylcamptothecin; and
(b) cisplatinum, wherein the proliferative disease is non-small cell lung cancer or ovarian cancer and wherein 7-t-butoxyiminomethylcamptothecin is administered followed by cis-platinum.

7. A method for treating a proliferative disease comprising administering pharmaceutically and synergistically effective amounts of a combination of:
(a) 7-t-butoxyiminomethylcamptothecin; and
(b) carboplatin, wherein the proliferative disease is selected from the group consisting of ovarian cancer and non-small cell lung cancer and the administration is simultaneous, concurrent, separate or sequential.

8. A method for treating a proliferative disease comprising administering pharmaceutically and synergistically effective amounts of a combination of:
(a) 7-t-butoxyiminomethylcamptothecin; and
(b) {6-[4-(4-ethyl-piperazin-1-ylmethyl)-phenyl]-7H-pyrrolo[2,3-d]pyrimidin-4-yl]-((R)-1-phenyl-ethyl)-amine, wherein the proliferative disease is selected from lung cancer, melanoma, renal cell adenocarcinoma, ovary adenocarcinoma, renal cell adenocarcinoma, pancreas epithelioid carcinoma, myeloma, colorectal adenocarcinoma, cervical carcinoma and pancreatic carcinoma, and the administration is simultaneous, concurrent, separate or sequential.

9. A method for treating a proliferative disease comprising administering pharmaceutically and synergistically effective amounts of a combination of:
(a) 7-t-butoxyiminomethylcamptothecin; and
(b) everolimus, wherein the proliferative disease is selected from the group consisting of non-small cell lung cancer, ovary adenocarcinoma, pancreas epithelioid carcinoma and colorectal adenocarcinoma, and the administration is simultaneous, concurrent, separate or sequential.

10. A method for treating a proliferative disease comprising administering pharmaceutically and synergistically effective amounts of a combination of:
(a) 7-t-butoxyiminomethylcamptothecin; and
(b) imatinib, wherein the proliferative disease is selected from the group consisting of non-small cell lung cancer, ovary adenocarcinoma, renal cell adenocarcinoma, pancreatic carcinoma, pancreas epithelioid carcinoma and colorectal adenocarcinoma, and the administration is simultaneous, concurrent, separate or sequential.

11. A method for treating a proliferative disease comprising administering pharmaceutically and synergistically effective amounts of a combination of:
(a) 7-t-butoxyiminomethylcamptothecin; and
(b) bortezomib, wherein the proliferative disease is ovary adenocarcinoma, melanoma and colorectal adenocarcinoma, and the administration is simultaneous, concurrent, separate or sequential.

\* \* \* \* \*